United States Patent
Hansen et al.

(10) Patent No.: US 11,654,043 B2
(45) Date of Patent: *May 23, 2023

(54) SENSOR ASSEMBLY PART AND A BASE PLATE FOR A MEDICAL APPLIANCE AND A METHOD FOR MANUFACTURING A BASE PLATE OR A SENSOR ASSEMBLY PART

(71) Applicant: Coloplast A/S, Humlebaek (DK)

(72) Inventors: Jais Ask Hansen, Jaegerspris (DK); Niels Hvid, Vedbaek (DK); Finn Speiermann, Virum (DK)

(73) Assignee: Coloplast A/S, Humlebaek (DK)

( * ) Notice: Subject to any disclaimer, the term of this patent is extended or adjusted under 35 U.S.C. 154(b) by 346 days.

This patent is subject to a terminal disclaimer.

(21) Appl. No.: 16/954,526

(22) PCT Filed: Dec. 20, 2018

(86) PCT No.: PCT/DK2018/050399
§ 371 (c)(1),
(2) Date: Jun. 17, 2020

(87) PCT Pub. No.: WO2019/120443
PCT Pub. Date: Jun. 27, 2019

(65) Prior Publication Data
US 2021/0085511 A1    Mar. 25, 2021

(51) Int. Cl.
*A61F 5/443* (2006.01)
*A61F 5/445* (2006.01)
*A61B 5/00* (2006.01)

(52) U.S. Cl.
CPC ............ *A61F 5/443* (2013.01); *A61B 5/4851* (2013.01); *A61B 5/6833* (2013.01); *A61F 5/445* (2013.01)

(58) Field of Classification Search
CPC ........ A61F 5/443; A61F 5/445; A61B 5/4851; A61B 5/6833
See application file for complete search history.

(56) References Cited

U.S. PATENT DOCUMENTS 2,327,514 A * 8/1943 Fenwick ................. A61F 5/445
604/338
2,542,233 A * 2/1951 Carroll ................... A61F 5/445
604/337

(Continued)

FOREIGN PATENT DOCUMENTS

CN   203786580 U   8/2014
CN   104902399 A   9/2015

(Continued)

*Primary Examiner* — Guy K Townsend
(74) *Attorney, Agent, or Firm* — Coloplast Corp., Coloplast A/S; Nick Baumann

(57) ABSTRACT

Disclosed is a base plate and a method for manufacturing a base plate. The method comprising: positioning a coupling part, the coupling part defining a terminal interface region; positioning an electrode assembly; positioning one or more terminal elements such that a distal part of each of the one or more terminal elements extends into the terminal interface region and a proximal part of each of the one or more terminal elements extends to the proximal side of the electrode assembly; affixing the proximal part of each of the one or more terminal elements to respective connection parts of the one or more electrodes; and securing the distal part of each of the one or more terminal elements to the coupling part.

17 Claims, 13 Drawing Sheets

(56) References Cited

U.S. PATENT DOCUMENTS

| | | | |
|---|---|---|---|
| 2,544,579 A * | 3/1951 | Ardner | A61F 5/445 604/337 |
| 3,214,502 A | 10/1965 | Schaar | |
| 3,832,510 A | 8/1974 | Pfau et al. | |
| 3,915,171 A | 10/1975 | Shermeta | |
| 3,941,133 A | 3/1976 | Chen | |
| 4,372,308 A | 2/1983 | Steer et al. | |
| 4,449,970 A | 5/1984 | Bevan et al. | |
| 4,668,227 A | 5/1987 | Kay | |
| 4,754,264 A | 6/1988 | Okada et al. | |
| 4,775,374 A | 10/1988 | Cilento et al. | |
| 4,982,742 A | 1/1991 | Claude | |
| 5,016,645 A | 5/1991 | Williams et al. | |
| 5,051,259 A | 9/1991 | Olsen et al. | |
| 5,074,851 A | 12/1991 | Plass et al. | |
| 5,111,812 A | 5/1992 | Swanson et al. | |
| 5,167,650 A | 12/1992 | Johnsen et al. | |
| 5,237,995 A | 8/1993 | Cano | |
| 5,318,543 A | 6/1994 | Ross et al. | |
| 5,358,488 A | 10/1994 | Suriyapa | |
| 5,486,158 A | 1/1996 | Samuelsen | |
| 5,570,082 A | 10/1996 | Maghereftch et al. | |
| 5,593,397 A | 1/1997 | La Gro | |
| 5,672,163 A * | 9/1997 | Ferreira | A61F 5/441 604/333 |
| 5,677,221 A | 10/1997 | Tseng | |
| 5,704,905 A | 1/1998 | Jensen et al. | |
| 5,790,036 A | 8/1998 | Fisher et al. | |
| 5,800,415 A | 9/1998 | Olsen | |
| 5,816,252 A | 10/1998 | Faries, Jr. et al. | |
| 5,834,009 A | 11/1998 | Sawers et al. | |
| 5,879,292 A | 3/1999 | Sternberg et al. | |
| 5,942,186 A | 8/1999 | Sanada et al. | |
| 6,015,399 A | 1/2000 | Mracna et al. | |
| 6,025,725 A | 2/2000 | Gerschenfeld et al. | |
| 6,057,689 A | 5/2000 | Saadat | |
| 6,103,033 A | 8/2000 | Say et al. | |
| 6,135,986 A * | 10/2000 | Leisner | A61F 5/441 604/324 |
| 6,171,289 B1 * | 1/2001 | Millot | A61F 5/443 604/336 |
| 6,206,864 B1 | 3/2001 | Kavanagh et al. | |
| 6,407,308 B1 | 6/2002 | Roe et al. | |
| 6,433,244 B1 | 8/2002 | Roe et al. | |
| 6,482,491 B1 | 11/2002 | Samuelsen et al. | |
| 6,485,476 B1 | 11/2002 | Von Dyck et al. | |
| 6,659,989 B1 | 12/2003 | Otto | |
| 6,764,474 B2 | 7/2004 | Nielsen et al. | |
| 7,066,919 B1 | 6/2006 | Sauerland et al. | |
| 7,150,728 B2 | 12/2006 | Hansen et al. | |
| 7,166,091 B1 * | 1/2007 | Zeltner | A61F 5/445 604/338 |
| 7,199,501 B2 | 4/2007 | Pei et al. | |
| 7,214,217 B2 | 5/2007 | Pedersen et al. | |
| 7,326,190 B2 * | 2/2008 | Botten | A61F 5/441 604/332 |
| 7,341,578 B2 * | 3/2008 | Bulow | A61F 5/441 604/338 |
| 7,367,965 B2 * | 5/2008 | Poulsen | A61F 5/441 604/324 |
| 7,559,922 B2 * | 7/2009 | Botten | A61F 5/441 604/332 |
| 7,625,362 B2 * | 12/2009 | Boehringer | A61M 1/90 604/304 |
| 7,641,612 B1 | 1/2010 | McCall | |
| 7,670,289 B1 | 3/2010 | McCall | |
| 7,943,812 B2 | 5/2011 | Stroebeck et al. | |
| 7,981,098 B2 * | 7/2011 | Boehringer | A61M 1/90 604/319 |
| 3,061,360 A1 | 11/2011 | Locke et al. | |
| 8,277,427 B2 | 10/2012 | Edvardsen et al. | |
| 8,319,003 B2 | 11/2012 | Olsen et al. | |
| 8,398,575 B1 | 3/2013 | McCall | |
| 8,398,603 B2 * | 3/2013 | Thirstrup | A61B 5/746 602/41 |
| 8,399,732 B2 | 3/2013 | Oelund et al. | |
| 8,409,158 B2 * | 4/2013 | Edvardsen | A61F 5/443 604/335 |
| 8,449,471 B2 | 5/2013 | Tran | |
| 8,500,718 B2 | 8/2013 | Locke et al. | |
| 8,632,492 B2 | 1/2014 | Delegge | |
| 8,680,991 B2 | 3/2014 | Tran | |
| 8,684,982 B2 * | 4/2014 | Nguyen-DeMary | A61F 5/441 604/327 |
| 8,740,865 B2 | 6/2014 | Krystek et al. | |
| 8,795,257 B2 | 8/2014 | Coulthard et al. | |
| 8,821,464 B2 | 9/2014 | Hanuka et al. | |
| 8,975,465 B2 | 3/2015 | Hong et al. | |
| 9,046,085 B2 | 6/2015 | Schoess et al. | |
| 9,066,812 B2 * | 6/2015 | Edvardsen | A61F 5/443 |
| 9,216,104 B2 * | 12/2015 | Thirstrup | A61F 13/02 |
| 9,308,332 B2 * | 4/2016 | Heppe | A61M 1/3656 |
| 9,322,797 B1 | 4/2016 | Lastinger et al. | |
| 9,629,964 B2 | 4/2017 | Wuepper | |
| 9,693,908 B2 | 7/2017 | Eriksson et al. | |
| 9,770,359 B2 | 9/2017 | Edvardsen et al. | |
| 9,788,991 B2 | 10/2017 | Bird | |
| 9,867,934 B2 | 1/2018 | Heppe | |
| 9,928,341 B2 * | 3/2018 | Angelides | G16H 40/67 |
| 10,016,298 B2 * | 7/2018 | Thirstrup | A61F 13/42 |
| D826,740 S | 8/2018 | Stevens et al. | |
| 10,500,084 B2 * | 12/2019 | Hansen | A61B 5/6843 |
| 10,531,977 B2 * | 1/2020 | Schoess | A61F 5/445 |
| 10,646,370 B2 * | 5/2020 | Keleny | A61F 5/441 |
| 10,792,184 B2 | 10/2020 | Hvid et al. | |
| 10,799,385 B2 * | 10/2020 | Hansen | A61F 5/4404 |
| 10,849,781 B2 * | 12/2020 | Hansen | A61F 5/445 |
| 10,874,541 B2 * | 12/2020 | Seres | A61B 5/002 |
| 10,987,243 B2 * | 4/2021 | Thirstrup | A61B 5/746 |
| 11,096,818 B2 * | 8/2021 | Thirstrup | A61F 13/02 |
| 11,135,084 B2 * | 10/2021 | Seres | A61B 5/14539 |
| 11,406,525 B2 * | 8/2022 | Seres | A61B 5/14539 |
| 11,471,318 B2 * | 10/2022 | Hansen | A61F 5/448 |
| 2002/0019615 A1 | 2/2002 | Roe et al. | |
| 2003/0132763 A1 | 7/2003 | Ellenz | |
| 2003/0169032 A1 | 9/2003 | Minchole et al. | |
| 2004/0030305 A1 | 2/2004 | Sakamoto | |
| 2004/0036484 A1 | 2/2004 | Tamai | |
| 2004/0049145 A1 | 3/2004 | Flick | |
| 2004/0078219 A1 | 4/2004 | Kaylor et al. | |
| 2004/0100376 A1 | 5/2004 | Lye et al. | |
| 2004/0111072 A1 | 6/2004 | McKissick | |
| 2004/0133175 A1 | 7/2004 | Hagedorn-Olsen | |
| 2004/0171999 A1 | 9/2004 | Andersen et al. | |
| 2004/0216833 A1 | 11/2004 | Fleming et al. | |
| 2005/0054997 A1 | 3/2005 | Buglino et al. | |
| 2005/0065488 A1 | 3/2005 | Elliott | |
| 2005/0070863 A1 * | 3/2005 | Bulow | A61F 5/441 604/332 |
| 2005/0085779 A1 * | 4/2005 | Poulsen | A61F 5/441 604/332 |
| 2005/0101841 A9 | 5/2005 | Kaylor et al. | |
| 2005/0240163 A1 | 10/2005 | Andersen | |
| 2005/0261645 A1 * | 11/2005 | Conrad | A61F 5/445 604/332 |
| 2006/0015081 A1 | 1/2006 | Suzuki et al. | |
| 2006/0025727 A1 * | 2/2006 | Boehringer | A61M 1/74 604/313 |
| 2006/0052752 A1 | 3/2006 | McMichael | |
| 2006/0194324 A1 | 8/2006 | Faries, Jr. et al. | |
| 2006/0271002 A1 * | 11/2006 | Botten | A61F 5/441 604/339 |
| 2007/0035405 A1 | 2/2007 | Wada et al. | |
| 2007/0135782 A1 | 6/2007 | Bager et al. | |
| 2007/0185464 A1 | 8/2007 | Fattman et al. | |
| 2008/0071214 A1 | 3/2008 | Locke et al. | |
| 2008/0075934 A1 | 3/2008 | Barlow, Jr. et al. | |
| 2008/0091154 A1 * | 4/2008 | Botten | A61F 5/441 96/155 |
| 2008/0140057 A1 | 6/2008 | Wood et al. | |
| 2008/0234641 A1 | 9/2008 | Locke et al. | |

(56) References Cited

U.S. PATENT DOCUMENTS

| | | | |
|---|---|---|---|
| 2008/0275327 A1* | 11/2008 | Faarbaek | A61B 5/68335 600/382 |
| 2008/0278337 A1 | 11/2008 | Huang et al. | |
| 2008/0300559 A1 | 12/2008 | Gustafson et al. | |
| 2008/0306459 A1 | 12/2008 | Albrectsen | |
| 2009/0012501 A1* | 1/2009 | Boehringer | A61M 1/82 604/543 |
| 2009/0118600 A1 | 5/2009 | Ortiz et al. | |
| 2009/0118687 A1 | 5/2009 | Kristensen et al. | |
| 2009/0167286 A1 | 7/2009 | Naylor et al. | |
| 2009/0173935 A1 | 7/2009 | Cho et al. | |
| 2009/0227969 A1 | 9/2009 | Jaeb et al. | |
| 2009/0247970 A1* | 10/2009 | Keleny | B01D 46/0036 156/247 |
| 2010/0010460 A1* | 1/2010 | Butler | A61F 5/441 604/333 |
| 2010/0030167 A1* | 2/2010 | Thirstrup | A61F 5/4404 340/657 |
| 2010/0036206 A1 | 2/2010 | Lorio | |
| 2010/0072271 A1 | 3/2010 | Thorstensson | |
| 2011/0034890 A1 | 2/2011 | Stroebech et al. | |
| 2011/0077497 A1 | 3/2011 | Oster et al. | |
| 2011/0130642 A1 | 6/2011 | Jaeb et al. | |
| 2012/0013130 A1 | 1/2012 | Jung | |
| 2012/0143154 A1* | 6/2012 | Edvardsen | A61F 5/4404 604/336 |
| 2012/0143155 A1* | 6/2012 | Edvardsen | A61F 5/443 604/318 |
| 2012/0253224 A1 | 10/2012 | Mir et al. | |
| 2012/0258302 A1 | 10/2012 | Hunt et al. | |
| 2012/0259230 A1 | 10/2012 | Riley | |
| 2012/0283678 A1* | 11/2012 | Nguyen-DeMary | A61F 5/445 604/338 |
| 2013/0018231 A1 | 1/2013 | Hong et al. | |
| 2013/0030167 A1 | 1/2013 | Wang et al. | |
| 2013/0030397 A1 | 1/2013 | Sabeti | |
| 2013/0060213 A1 | 3/2013 | Hanuka et al. | |
| 2013/0066285 A1 | 3/2013 | Locke et al. | |
| 2013/0072886 A1* | 3/2013 | Schertiger | A61F 5/445 604/335 |
| 2013/0102979 A1 | 4/2013 | Coulthard et al. | |
| 2013/0138065 A1 | 5/2013 | Buus | |
| 2013/0150769 A1 | 6/2013 | Heppe | |
| 2013/0165862 A1 | 6/2013 | Griffith et al. | |
| 2013/0192604 A1* | 8/2013 | Persson | A61M 16/047 128/207.16 |
| 2013/0226116 A1 | 8/2013 | Edvardsen et al. | |
| 2013/0231620 A1* | 9/2013 | Thirstrup | A61F 5/445 604/344 |
| 2013/0261575 A1 | 10/2013 | Kiyoshi | |
| 2013/0303867 A1 | 11/2013 | Elfstrom et al. | |
| 2013/0324952 A1 | 12/2013 | Krystek et al. | |
| 2014/0051946 A1 | 2/2014 | Arne et al. | |
| 2014/0200538 A1 | 7/2014 | Euliano et al. | |
| 2014/0236111 A1 | 8/2014 | Casado et al. | |
| 2014/0236335 A1 | 8/2014 | Lewis et al. | |
| 2014/0275854 A1 | 9/2014 | Venkatraman et al. | |
| 2014/0276501 A1* | 9/2014 | Cisko | A61F 5/443 604/355 |
| 2014/0288381 A1* | 9/2014 | Faarbaek | A61B 5/0002 600/300 |
| 2014/0323909 A1 | 10/2014 | Kim | |
| 2014/0327433 A1 | 11/2014 | Anway et al. | |
| 2014/0336493 A1 | 11/2014 | Kulach et al. | |
| 2015/0231802 A1 | 8/2015 | Quan et al. | |
| 2015/0250639 A1* | 9/2015 | Thirstrup | A61F 13/00051 156/278 |
| 2015/0257923 A1* | 9/2015 | Thirstrup | A61F 13/42 604/318 |
| 2015/0342777 A1 | 12/2015 | Seres et al. | |
| 2015/0374896 A1 | 12/2015 | Du et al. | |
| 2016/0084869 A1 | 3/2016 | Yuen et al. | |
| 2016/0158056 A1 | 6/2016 | Davis et al. | |
| 2016/0158969 A1 | 6/2016 | McLane et al. | |
| 2016/0166438 A1* | 6/2016 | Rovaniemi | A61F 13/42 493/320 |
| 2016/0218555 A1 | 7/2016 | Slaby et al. | |
| 2016/0235581 A1* | 8/2016 | Keleny | A61F 5/441 |
| 2016/0278990 A1 | 9/2016 | Chen | |
| 2016/0284084 A1 | 9/2016 | Gurcan et al. | |
| 2016/0305776 A1 | 10/2016 | Martensson et al. | |
| 2016/0310140 A1 | 10/2016 | Belson et al. | |
| 2016/0310329 A1 | 10/2016 | Patel et al. | |
| 2016/0361015 A1 | 12/2016 | Wang et al. | |
| 2017/0042614 A1 | 2/2017 | Salahieh et al. | |
| 2017/0050004 A1 | 2/2017 | Tilson et al. | |
| 2017/0055896 A1 | 3/2017 | Al-Ali et al. | |
| 2017/0079576 A1 | 3/2017 | Stroebech et al. | |
| 2017/0112658 A1 | 4/2017 | Hosono | |
| 2017/0140103 A1* | 5/2017 | Angelides | A61F 5/4404 |
| 2017/0156920 A1 | 6/2017 | Hunt et al. | |
| 2017/0262986 A1 | 9/2017 | Xiong et al. | |
| 2017/0340474 A1* | 11/2017 | Thirstrup | A61B 5/746 |
| 2017/0348137 A1 | 12/2017 | Hvid et al. | |
| 2017/0360592 A1 | 12/2017 | Carrubba | |
| 2018/0049667 A1 | 2/2018 | Heppe | |
| 2018/0055359 A1 | 3/2018 | Shamim et al. | |
| 2018/0171183 A1 | 6/2018 | Sakurai et al. | |
| 2019/0133810 A1* | 5/2019 | Seres | A61F 5/4404 |
| 2019/0133811 A1* | 5/2019 | Seres | A61F 5/4404 |
| 2019/0133812 A1* | 5/2019 | Seres | A61F 5/448 |
| 2019/0142623 A1* | 5/2019 | Schoess | A61F 5/4404 604/336 |
| 2019/0175386 A1* | 6/2019 | Monty | A61F 5/445 |
| 2019/0192066 A1 | 6/2019 | Schoess et al. | |
| 2019/0192332 A1* | 6/2019 | Hansen | A61B 5/7475 |
| 2019/0192333 A1* | 6/2019 | Hansen | A61F 5/445 |
| 2019/0192334 A1* | 6/2019 | Hansen | G01M 3/40 |
| 2019/0240059 A1 | 8/2019 | Seres et al. | |
| 2019/0247050 A1* | 8/2019 | Goldsmith | A61F 2/82 |
| 2019/0374163 A1* | 12/2019 | Faarbaek | A61B 5/6833 |
| 2019/0374372 A1* | 12/2019 | Seres | A61B 5/6802 |
| 2020/0100931 A1 | 4/2020 | Schoess et al. | |
| 2020/0188161 A1* | 6/2020 | Seres | G01K 13/00 |
| 2020/0246174 A1* | 8/2020 | Hansen | A61F 5/443 |
| 2020/0246175 A1* | 8/2020 | Hansen | G01M 3/16 |
| 2020/0246176 A1* | 8/2020 | Hansen | A61F 5/445 |
| 2020/0246177 A1* | 8/2020 | Hansen | A61B 5/4851 |
| 2020/0276063 A1 | 9/2020 | Herencia | |
| 2020/0306074 A1* | 10/2020 | Speiermann | A61F 5/4404 |
| 2020/0330258 A1* | 10/2020 | Hansen | A61F 13/15577 |
| 2020/0330260 A1* | 10/2020 | Hansen | A61F 5/4404 |
| 2020/0337880 A1* | 10/2020 | Hansen | A61F 5/44 |
| 2020/0337881 A1* | 10/2020 | Hansen | A61F 5/443 |
| 2020/0337882 A1* | 10/2020 | Hansen | A61F 5/445 |
| 2020/0337883 A1* | 10/2020 | Hansen | A61F 5/443 |
| 2020/0375499 A1* | 12/2020 | Hansen | A61B 5/6833 |
| 2020/0375782 A1 | 12/2020 | Hansen et al. | |
| 2020/0375783 A1 | 12/2020 | Hansen et al. | |
| 2020/0375784 A1* | 12/2020 | Hansen | A61F 5/445 |
| 2020/0375785 A1* | 12/2020 | Hansen | A61F 5/443 |
| 2020/0375786 A1* | 12/2020 | Hansen | A61F 5/443 |
| 2020/0383637 A1* | 12/2020 | Hansen | A61B 5/7455 |
| 2020/0383818 A1* | 12/2020 | Hansen | A61F 5/443 |
| 2020/0383819 A1* | 12/2020 | Sletten | A61F 5/443 |
| 2020/0383820 A1* | 12/2020 | Hansen | A61F 5/445 |
| 2020/0383821 A1* | 12/2020 | Hansen | A61F 5/4404 |
| 2020/0390587 A1* | 12/2020 | Svanegaard | A61F 5/4404 |
| 2020/0390588 A1* | 12/2020 | Hansen | A61F 5/4404 |
| 2020/0390589 A1* | 12/2020 | Hansen | A61F 5/443 |
| 2020/0395120 A1* | 12/2020 | Svanegaard | A61B 5/4255 |
| 2020/0395610 A1 | 12/2020 | Ono et al. | |
| 2020/0405228 A1* | 12/2020 | Svanegaard | A61B 5/002 |
| 2020/0405229 A1* | 12/2020 | Svanegaard | A61B 5/6833 |
| 2020/0405230 A1* | 12/2020 | Svanegaard | A61B 5/742 |
| 2021/0000414 A1* | 1/2021 | Svanegaard | A61B 5/4851 |
| 2021/0000633 A1* | 1/2021 | Hansen | A61B 5/4851 |
| 2021/0000634 A1* | 1/2021 | Svanegaard | A61B 5/0022 |
| 2021/0000635 A1 | 1/2021 | Hansen et al. | |
| 2021/0000636 A1 | 1/2021 | Hansen et al. | |
| 2021/0007663 A1* | 1/2021 | Svanegaard | A61B 5/742 |
| 2021/0007881 A1* | 1/2021 | Svanegaard | A61F 5/4404 |
| 2021/0015653 A1 | 1/2021 | Hansen et al. | |

(56) References Cited

U.S. PATENT DOCUMENTS

| | | | |
|---|---|---|---|
| 2021/0015654 A1* | 1/2021 | Hansen | A61F 5/445 |
| 2021/0022683 A1 | 1/2021 | Faarbaek et al. | |
| 2021/0038424 A1* | 2/2021 | Svanegaard | A61B 5/6843 |
| 2021/0059603 A1* | 3/2021 | Svanegaard | A61F 5/4404 |
| 2021/0085511 A1* | 3/2021 | Hansen | A61B 5/6833 |
| 2021/0085512 A1* | 3/2021 | Hansen | A61F 5/445 |
| 2021/0100533 A1* | 4/2021 | Seres | A61F 5/441 |
| 2021/0177642 A1* | 6/2021 | Andersen | A61F 5/443 |
| 2021/0212855 A1* | 7/2021 | Hansen | A61B 5/6811 |
| 2021/0338471 A1* | 11/2021 | Nolan | A61F 5/4404 |
| 2021/0361464 A1* | 11/2021 | Larsen | A61F 5/443 |
| 2021/0361465 A1* | 11/2021 | Hansen | A61F 5/445 |
| 2021/0361466 A1 | 11/2021 | Hansen et al. | |
| 2021/0361467 A1* | 11/2021 | Hansen | A61B 5/1118 |
| 2021/0369197 A1* | 12/2021 | Hansen | A61B 5/7405 |
| 2021/0369488 A1* | 12/2021 | Hansen | A61F 5/445 |
| 2021/0369489 A1* | 12/2021 | Hansen | B29C 65/48 |
| 2021/0369490 A1* | 12/2021 | Hansen | A61F 5/443 |
| 2021/0386368 A1 | 12/2021 | Carlsson et al. | |
| 2022/0000652 A1* | 1/2022 | Thirstrup | A61F 5/443 |
| 2022/0031495 A1* | 2/2022 | Seres | A61B 5/01 |
| 2022/0079802 A1* | 3/2022 | Hansen | A61F 5/4404 |
| 2022/0079803 A1* | 3/2022 | Windeballe | A61F 5/445 |
| 2022/0087851 A1* | 3/2022 | Stroebech | A61F 5/4404 |
| 2022/0117771 A1* | 4/2022 | Fearn | A61F 5/449 |
| 2022/0142807 A1* | 5/2022 | Tofte | A61F 5/4404 |
| 2022/0192860 A1* | 6/2022 | Hansen | A61F 5/445 |
| 2022/0241104 A1* | 8/2022 | Knoedler | A61F 5/4404 |
| 2022/0241105 A1* | 8/2022 | Hansen | A61B 5/441 |
| 2022/0265457 A1* | 8/2022 | Emborg | A61F 5/445 |
| 2022/0265458 A1* | 8/2022 | Carlsson | A61F 5/443 |

FOREIGN PATENT DOCUMENTS

| | | | |
|---|---|---|---|
| CN | 104980878 A | 10/2015 | |
| CN | 105588856 A | 5/2016 | |
| CN | 206271160 U | 6/2017 | |
| CN | 206450708 U | 8/2017 | |
| DE | 3437950 A1 | 4/1985 | |
| DE | 3836590 A1 | 5/1990 | |
| DE | 19953062 A1 | 5/2000 | |
| DE | 19900611 C1 | 7/2000 | |
| DE | 102011014321 A1 | 9/2012 | |
| DE | 102011076219 A1 | 11/2012 | |
| EP | 0168967 A1 | 1/1986 | |
| EP | 0373782 A1 | 6/1990 | |
| EP | 0416397 A1 | 3/1991 | |
| EP | 0800804 A1 | 10/1997 | |
| EP | 1275357 A1 | 1/2003 | |
| EP | 1188157 B1 | 12/2005 | |
| EP | 2108345 A1 | 10/2009 | |
| EP | 2489561 A2 | 8/2012 | |
| EP | 2601915 A1 | 6/2013 | |
| EP | 2654646 B1 | 7/2016 | |
| EP | 3213727 A1 | 6/2017 | |
| EP | 3064179 B1 | 9/2021 | |
| GB | 2219679 A | 12/1989 | |
| GB | 2343628 A | 5/2000 | |
| GB | 2465742 A | 6/2010 | |
| GB | 2542093 A | 3/2017 | |
| JP | 2001087299 A2 | 4/2001 | |
| JP | 2002055074 A | 2/2002 | |
| JP | 2002224093 A | 8/2002 | |
| JP | 2005323981 A | 11/2005 | |
| JP | 2014033745 A | 2/2014 | |
| JP | 2014054368 A | 3/2014 | |
| KR | 20120003987 A | 1/2012 | |
| RU | 2527155 C2 | 8/2014 | |
| TW | 201201783 A | 1/2012 | |
| WO | 1994015562 A1 | 7/1994 | |
| WO | 1997010012 A1 | 3/1997 | |
| WO | 1999033037 A1 | 7/1999 | |
| WO | 1999036017 A1 | 7/1999 | |
| WO | 2000079497 A1 | 12/2000 | |
| WO | 2001013830 A1 | 3/2001 | |
| WO | 2001050996 A1 | 7/2001 | |
| WO | 2002052302 A2 | 7/2002 | |
| WO | 2002099765 A1 | 12/2002 | |
| WO | 2005082271 A2 | 9/2005 | |
| WO | 2006008866 A1 | 1/2006 | |
| WO | 2006094513 A2 | 9/2006 | |
| WO | 2007000168 A1 | 1/2007 | |
| WO | 2007059774 A2 | 5/2007 | |
| WO | 2007098762 A1 | 9/2007 | |
| WO | WO-2007098762 A1 * | 9/2007 | A61B 5/746 |
| WO | 2007133555 A2 | 11/2007 | |
| WO | 2008057884 A2 | 5/2008 | |
| WO | 2009006900 A1 | 1/2009 | |
| WO | 2009052496 A1 | 4/2009 | |
| WO | 2009112912 A2 | 9/2009 | |
| WO | 2011003421 A1 | 1/2011 | |
| WO | 2011004165 A1 | 1/2011 | |
| WO | 2011061540 A1 | 5/2011 | |
| WO | 2011105701 A2 | 9/2011 | |
| WO | 2011123018 A1 | 10/2011 | |
| WO | 2011139499 A1 | 11/2011 | |
| WO | 2011161254 A2 | 12/2011 | |
| WO | 2012068386 A1 | 5/2012 | |
| WO | 2012076022 A2 | 6/2012 | |
| WO | 2013013197 A1 | 1/2013 | |
| WO | 2014004207 A1 | 1/2014 | |
| WO | 2014086369 A1 | 6/2014 | |
| WO | 2015007284 A1 | 1/2015 | |
| WO | 2015014774 A1 | 2/2015 | |
| WO | 2015084462 A1 | 6/2015 | |
| WO | 2015094064 A1 | 6/2015 | |
| WO | 2016166731 A1 | 10/2016 | |
| WO | 2017023794 A1 | 2/2017 | |
| WO | 2017062042 A1 | 4/2017 | |
| WO | 2017067558 A1 | 4/2017 | |
| WO | 2017067560 A1 | 4/2017 | |
| WO | 2017088153 A1 | 6/2017 | |
| WO | 2017136696 A1 | 8/2017 | |
| WO | 2017190752 A1 | 11/2017 | |
| WO | 2018028756 A1 | 2/2018 | |
| WO | 2019094635 A1 | 5/2019 | |
| WO | 2019161863 A1 | 8/2019 | |

* cited by examiner

SENSOR ASSEMBLY PART AND A BASE PLATE FOR A MEDICAL APPLIANCE AND A METHOD FOR MANUFACTURING A BASE PLATE OR A SENSOR ASSEMBLY PART

The present disclosure relates to an ostomy system, devices thereof, method of manufacturing and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
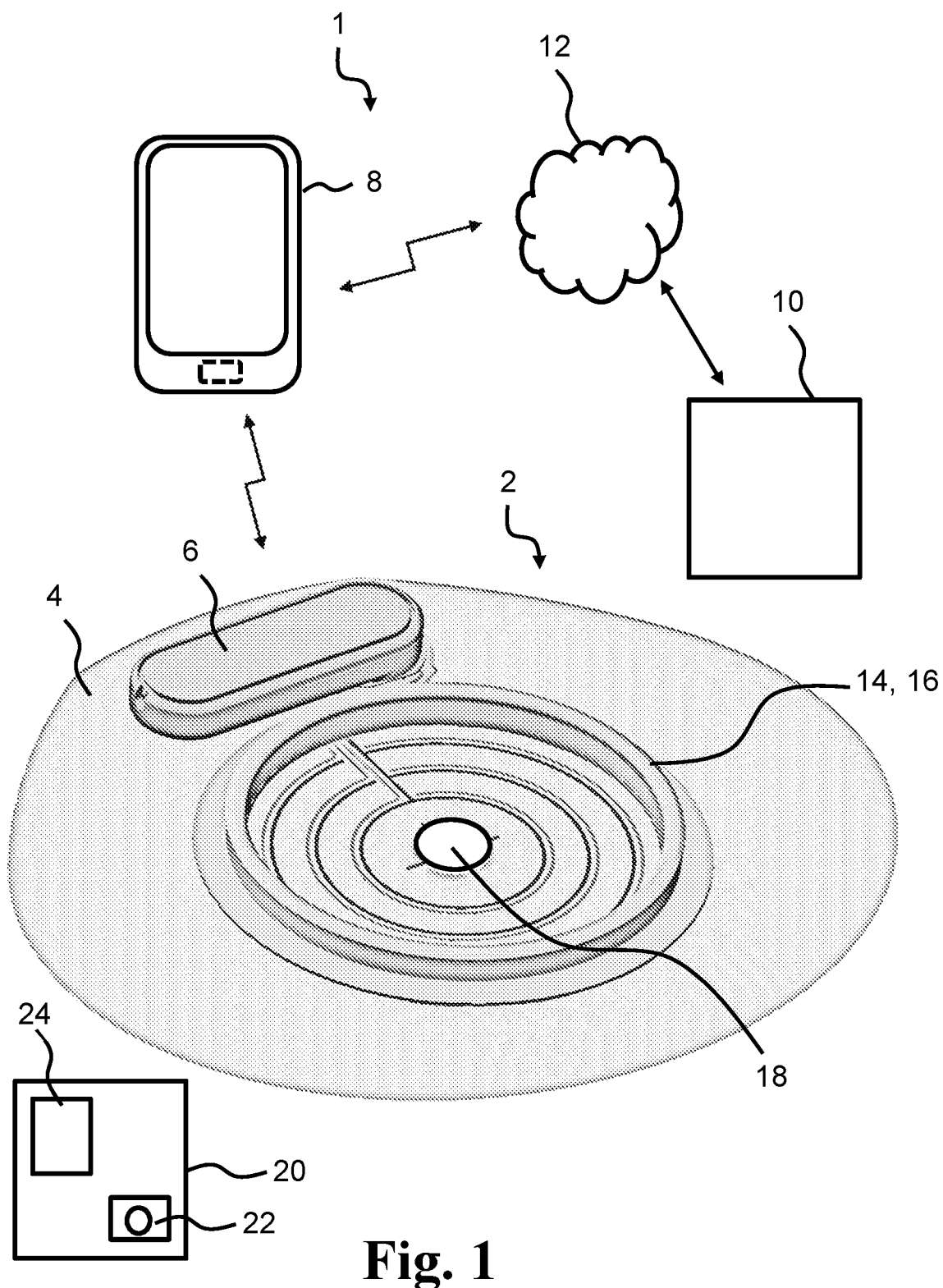
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocoloids.

The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be a second adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocoloids.

The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part may comprise a monitor interface. The monitor interface may be configured for electrically and/or mechanically connecting the ostomy appliance (base plate/sensor assembly part) to the monitor device. The monitor interface may be configured for wirelessly connecting the ostomy appliance (base plate/sensor assembly part) to the monitor device. Thus, the monitor interface of the base plate and/or the sensor assembly part may be configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as of the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening, e.g. with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates and/or sensor assembly parts, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value.

The first threshold set may comprise a first tertiary threshold value.

The first criteria set may be given by
($P\_1\_1 < TH\_1\_1$),
($P\_2\_1 > TH\_1\_2$), and
($P\_3\_1 > TH\_1\_3$),
wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate. The first threshold values ($TH\_1\_1$, $TH\_1\_2$ and $TH\_1\_3$) may be the same or different, e.g. depending on the electrode configuration of the base plate and/or the sensor assembly part. The first tertiary criterion ($P\_3\_1 < TH\_1\_3$) may be omitted in the first criteria set.

The first primary parameter $P\_1\_1$ may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by
($P\_1\_1 < TH\_2\_1$),
($P\_2\_1 > TH\_2\_2$), and
($P\_3\_1 > TH\_2\_3$),
wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate. The second threshold values ($TH\_2\_1$, $TH\_2\_2$ and $TH\_2\_3$) may be the same or different, e.g. depending on the electrode configuration of the base plate and/or the sensor assembly part. The second primary criterion ($P\_1\_1 < TH\_2\_1$) and/or the second tertiary criterion ($P\_3\_1 > TH\_2\_3$) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by
($P\_1\_1 > TH\_D\_1$),
($P\_2\_1 > TH\_D\_2$), and
($P\_3\_1 > TH\_D\_3$)
wherein $P\_1\_1$ is a first primary parameter based on the first parameter data and indicative of the resistance between the first electrode pair, $TH\_D\_1$ is a default primary threshold value, $P\_2\_1$ is a second primary parameter based on the second parameter data and indicative of the resistance between the second electrode pair, $TH\_D\_2$ is a default secondary threshold value, $P\_3\_1$ is a third primary parameter based on the third parameter data and indicative of the resistance between the third electrode pair, $TH\_D\_3$ is a default tertiary threshold value, and wherein the default operating state is indicative of very low or no degree of radial erosion on the base plate. The default threshold values ($TH\_D\_1$, $TH\_D\_2$ and $TH\_D\_3$) may be the same or different, e.g. depending on the electrode configuration of the base plate and/or the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by
($P\_1\_1 < TH\_3\_1$),
($P\_2\_1 > TH\_3\_2$), and
($P\_3\_1 > TH\_3\_3$),
wherein $P\_1\_1$ is a first primary parameter based on the first parameter data and indicative of the resistance between the first electrode pair, $TH\_3\_1$ is a third primary threshold value, $P\_2\_1$ is a second primary parameter based on the second parameter data and indicative of the resistance between the second electrode pair, $TH\_3\_2$ is a third secondary threshold value, $P\_3\_1$ is a third primary parameter based on the third parameter data and indicative of the resistance between the third electrode pair, $TH\_3\_3$ is a third tertiary threshold value, and wherein the third operating state is indicative of high degree of radial erosion on the base plate. The third threshold values ($TH\_3\_1$, $TH\_3\_2$ and $TH\_3\_3$) may be the same or different, e.g. depending on the electrode configuration of the base plate and/or the sensor assembly part. The third primary criterion ($P\_1\_1 < TH\_3\_1$) and/or the third secondary criterion ($P\_2\_1 < TH\_3\_2$) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by
($P\_4\_1 < TH\_4\_4$)
wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a method for manufacturing a base plate or a sensor assembly part, such as a base plate or a sensor assembly part for an ostomy appliance, such as a base plate or a sensor assembly part as disclosed above.

The method comprises positioning a coupling part, such as base plate coupling part or a sensor assembly coupling part, e.g. a coupling part for the monitor interface of the base plate or the sensor assembly part. The coupling part defines a terminal interface region. The terminal interface region may be a region wherein terminals, e.g. of the base plate and/or sensor assembly part, may connect, such as mechanically and/or electrically connect, with respective terminals of a monitor device.

The method further comprises positioning an electrode assembly, such as the electrode assembly as disclosed above. The electrode assembly has a distal side and a proximal side. The electrode assembly and/or the coupling part is positioned such that the distal side of the electrode assembly is facing the coupling part. The electrode assembly comprises a support layer and one or more electrodes provided, such as formed, on a proximal side of the support layer. Each of the one or more electrodes comprises a connection part.

The method comprises positioning one or more terminal elements such that a distal part of each of the one or more terminal elements extends into the terminal interface region and a proximal part of each of the one or more terminal elements extends to the proximal side of the electrode assembly.

The method comprises affixing the proximal part of each of the one or more terminal elements to respective connection parts of the one or more electrodes. The proximal parts and the connection parts may be affixed by bonding each of the one or more terminal elements together with respective connection parts of the one or more electrodes. Affixing the proximal parts to the connection parts may be understood as the proximal parts and the connection part being essentially inseparable. For example, the proximal parts and the connection parts may be glued together or soldered together, or similar. For example, the proximal parts and the connection parts may be affixed such that connection, such as electrical connection, between the one or more terminal elements and respective connection parts is maintained even in the absence of external forces forcing the terminal elements and the respective connection parts together.

Affixing the proximal part of each of the one or more terminal elements with the respective connection parts of the one or more electrodes, provides that the electrical connection between the one or more terminal elements and the electrodes are maintained, even if the material between the coupling part and the electrodes, e.g. due to viscous flow of material, becomes thinner over time. This may be particularly relevant, if a viscous material, such as an adhesive, is provided between the coupling part and the electrode assembly.

The method comprises securing the distal part of each of the one or more terminal elements to the coupling part. Securing the distal part to the coupling part may prevent axial movement of the terminal element in a proximal direction and/or in a distal direction relative to the coupling part.

A base plate for an ostomy appliance is also disclosed, such as a base plate manufactured by a method, such as the above-mentioned method. Also, a sensor assembly part for an ostomy appliance is disclosed, such as a sensor assembly part for being applied to a base plate, such as a sensor assembly part manufactured by a method, such as the previously disclosed method. The base plate and/or the sensor assembly part comprises a coupling part defining a terminal interface region; an electrode assembly having a distal side and a proximal side; and one or more terminal elements having a distal part and a proximal part. The terminal interface region may be a region wherein terminals, e.g. of the base plate and/or sensor assembly part, may connect, such as mechanically and/or electrically connect, with respective terminals of a monitor device.

The distal side of the electrode assembly is facing the coupling part. The electrode assembly comprises a support layer and one or more electrodes provided, such as formed, on a proximal side of the support layer. Each of the one or more electrodes comprises a connection part.

The distal part of each of the one or more terminal elements extends into the terminal interface region. The proximal part of each of the one or more terminal elements extends to the proximal side of the electrode assembly.

The proximal part of each of the one or more terminal elements are affixed to respective connection parts of the one or more electrodes. The proximal parts and the connection parts may be affixed by each of the one or more terminal elements and respective connection parts of the one or more electrodes being bonded together. The proximal parts and the connection parts being affixed may be understood as the proximal parts and the connection part being essentially inseparable. For example, the proximal parts and the connection parts may be glued together or soldered together, or similar.

The distal part of each of the one or more terminal elements are secured to the coupling part. For example, such as to prevent axial movement of the terminal element in a proximal direction and/or in a distal direction relative to the coupling part.

The base plate and/or the sensor assembly part may comprise a first adhesive layer, such as the first adhesive layer as disclosed above. The first adhesive layer may have a distal side facing the proximal side of the electrode assembly. The proximal part of each of the one or more terminals may be located between the first adhesive layer and the electrode assembly. The method may comprise positioning a first adhesive layer with a distal side facing the proximal side of the electrode assembly. The first adhesive layer may be positioned after positioning the one or more terminal elements. For example, such that the proximal part of each of the one or more terminal elements is located between the first adhesive layer and the electrode assembly.

A release liner may be provided on the proximal side of the first adhesive layer. The first adhesive layer may be formed on the release liner, e.g. by scraping a thin layer of a first adhesive composition onto the release liner to form the first adhesive layer. The first adhesive layer may be formed on the release liner prior to positioning the first adhesive layer, e.g. with the release liner.

The base plate and/or the sensor assembly part may comprise a second adhesive layer, such as the second adhesive layer as disclosed above. The second adhesive layer may have a distal side facing the coupling part. The second adhesive layer may have a proximal side facing the distal side of the electrode assembly. The method may comprise positioning a second adhesive layer with a distal side facing the coupling part and a proximal side facing the distal side of the electrode assembly.

The base plate and/or the sensor assembly part may comprise a top layer, such as the top layer as disclosed above. The top layer may have a distal side facing the coupling part and a proximal side facing the distal side of the second adhesive layer and/or the electrode assembly. The method may comprise positioning a top layer with a distal side facing the coupling part and a proximal side facing the distal side of the second adhesive layer and/or the electrode assembly.

The second adhesive layer may be formed on the top layer, such as on the proximal side of the top layer, e.g. after the top layer is positioned. The second adhesive layer may be provided on the top layer by scraping a thin layer of a second adhesive composition onto the top layer, such as on the proximal side of the top layer, to form the second adhesive layer.

The coupling part may be attached to the top layer. For example, the coupling part may be positioned on the distal side of the top layer and optionally the coupling part may be fixed, such as glued, soldered, or welded, to the top layer.

The one or more terminal elements may be inserted through one or more of the electrode assembly, the top layer and/or the second adhesive layer. For example, positioning the one or more terminal elements may comprise inserting the one or more terminal elements through the electrode assembly, the top layer and/or the second adhesive layer. For example, the one or more terminal elements may be used to penetrate the electrode assembly, the top layer and/or the second adhesive layer.

Using the terminal elements to penetrate layers may provide the advantage that specific tools are not needed to provide holes in the respective layers. This may, in particular, be an advantage if the layers to be penetrated comprise adhesive, because adhesive will have a tendency to stick to the tools, and thereby extensive cleaning or frequent exchange of the tools may be required. Using the terminal elements to penetrate the respective layers may prevent physical contact between production tools and layers, such as adhesive layers.

The one or more terminal elements may be inserted through the support layer of the electrode assembly. Inserting the one or more terminal elements may comprise inserting the one or more terminal elements through the support layer of the electrode assembly, such as inserting the one or more terminal elements through the support layer while not penetrating the one or more electrodes. A terminal element bend, such as the proximal terminal element bend may provide the proximal part of the terminal elements electrically connecting the respective connection parts of the one or more electrodes.

Alternatively, or additionally the one or more terminal elements may be inserted through the connection parts of the one or more electrodes. Inserting the one or more terminal elements may comprise inserting the one or more terminal elements through the respective connection parts of the one or more electrodes.

The one or more terminal elements may be inserted from either side. Inserting the one or more terminal elements may comprise inserting the one or more terminal elements from the proximal side of the electrode assembly. Inserting the one or more terminals elements may comprises inserting the one or more terminal elements from the distal side of the electrode assembly.

Each of the one or more terminal elements may comprise a proximal terminal element bend and/or a distal terminal element bend. The method may comprise providing each of the one or more terminal elements with a proximal terminal element bend and/or a distal terminal element bend. The proximal terminal element bend and/or the distal terminal element bend may be provided prior to affixing the proximal part of each of the one or more terminal elements to the respective connection parts of respective electrodes of the one or more electrodes. Alternatively, the proximal terminal element bend and/or the distal terminal element bend may be provided while affixing the proximal part of each of the one or more terminal elements to the respective connection parts of respective electrodes of the one or more electrodes. For example, the proximal terminal element bend may be provided such as to position the proximal part in contact with glue, e.g. conductive glue, to be affixed to the respective connection part.

A terminal element bend, such as a proximal terminal element bend and/or a distal terminal element bend may be provided to a terminal element by applying a force to an end, such as a proximal end or distal end, of the terminal element, e.g. after insertion of the terminal element, in a direction non-parallel with a longitudinal direction of the terminal element.

Alternatively or additionally, a distal terminal element bend of a terminal element may be provided by applying a force to the terminal element towards a distal end of the terminal element and parallel to a longitudinal direction of the terminal element, and guiding the distal end of the terminal element, e.g. by a guide groove, in a direction non-parallel with the longitudinal direction. Providing the distal terminal element bend by this method may be particularly advantageous if the terminal elements are inserted from the proximal side of the electrode assembly.

Similarly, a proximal terminal element bend of a terminal element may be provided by applying a force to the terminal element towards a proximal end of the terminal element and parallel to the longitudinal direction of the terminal element, and guiding the proximal end of the terminal element, e.g. by a guide groove, in a direction non-parallel with the longitudinal direction. Providing the proximal terminal element bend by this method may be particularly advantageous if the terminal elements are inserted from the distal side of the electrode assembly.

A terminal element bend, such as the proximal terminal element bend and/or the distal terminal element bend may form an angle, e.g. between 60-130 degrees, such as between 70-115 degrees, such as between 80-100 degrees. The angle of a terminal element bend, such as a proximal terminal element bend and/or a distal terminal element bend, may be defined relative to a straight terminal element, e.g. no bend has a 0 degrees angle and a U-shaped bend has a 180 degrees angle.

A terminal element bend, such as the proximal terminal element bend and/or the distal terminal element bend may be formed prior to positioning the one or more terminal elements. Alternatively or additionally, a terminal element bend, such as the proximal terminal element bend and/or the distal terminal element bend may be formed after positioning the one or more terminal elements.

A terminal element bend, such as the proximal terminal element bend and/or the distal terminal element bend may be provided with tension, e.g. such as to allow for a reduction of a distance between distal part and the proximal part of each of the one or more terminal elements, and/or to allow for a reduction of a distance between the coupling part and the connection parts of the electrode assembly.

Securing the distal part of the one or more terminal elements to the coupling part may comprise applying a force to the terminal elements in an axial direction, e.g. in a distal direction, while securing the distal part of each of the one or more terminal elements to the coupling part.

The distal part of each of the one or more terminal elements may contact a surface, such as a distal surface, of the coupling part. Securing the distal part of each of the one or more terminal elements to the coupling part may comprise positioning the distal part of each of the one or more terminal elements to contact a surface, such as a distal surface, of the coupling part. For example, each of the one or more terminal elements may be provided with a distal terminal element bend, e.g. to position the distal part of each of the one or more terminal elements to contact the surface of the coupling part. The method may comprise providing each of the one or more terminal elements with a distal terminal element bend e.g. to position the distal part of each of the one or more terminal elements to contact the surface of the coupling part. Positioning the distal part of each of the one or more terminal elements to contact a distal surface of the coupling part may facilitate a fastening of the coupling part towards the layers of the base plate and/or the sensor assembly part. Alternatively or additionally positioning the distal part of each of the one or more terminal elements to contact a distal surface of the coupling part may facilitate that the proximal part of each of the one or more terminal elements may be pulled towards their respective connection parts by pulling the coupling part in a distal direction.

The coupling part may be aligned with the connection parts of the one or more electrodes. For example, positioning the coupling part and/or positioning the electrode assembly may comprise aligning the coupling part with the connection part of the one or more electrodes. For example, the coupling part, such as the distal surface of the coupling part, may be positioned axially to the connection parts of the one or more electrodes.

The proximal part of each of the one or more terminal elements may be affixed to the respective connection parts with an affixing material, e.g. solder and/or glue, such as an electrically conductive glue. Affixing the proximal part of each of the one or more terminal elements to the respective connection parts of the one or more electrodes may comprise providing an affixing material, e.g. solder and/or glue, such as an electrically conductive glue, affixing the proximal part of each of the one or more terminal elements to the respective connection parts of the one or more electrodes. For example, a conductive glue may be provided between the proximal part of each of the one or more electrodes and the respective connection parts of the one or more electrodes of the electrode assembly. Affixing the proximal part of each of the one or more terminal elements to the respective connection parts of the one or more electrodes may comprise curing of the affixing material, e.g. uv-curing, thermal curing, etc.

Alternatively or additionally, the proximal part of each of the one or more terminal elements may be affixed to the respective connection parts with solder. Affixing the proximal part of each of the one or more terminal elements to the respective connection parts of the one or more electrodes may comprise soldering the proximal part of each of the one or more terminal elements to the respective connection parts of the one or more electrodes.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

Figure 2:
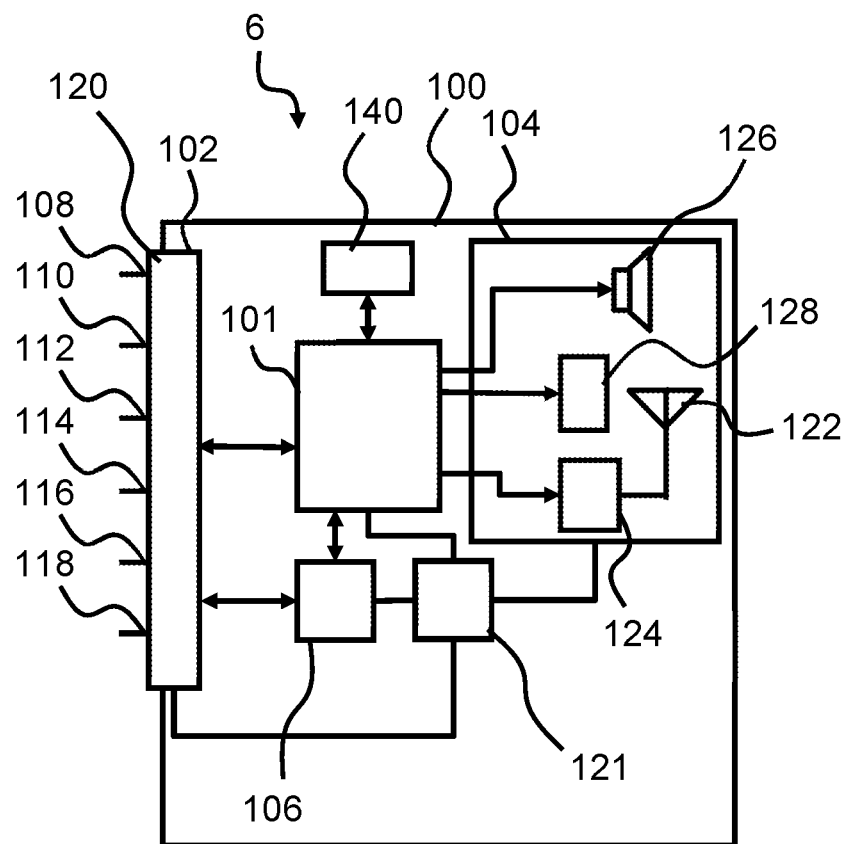
FIG. 2 illustrates an exemplary monitor device of the ostomy system.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
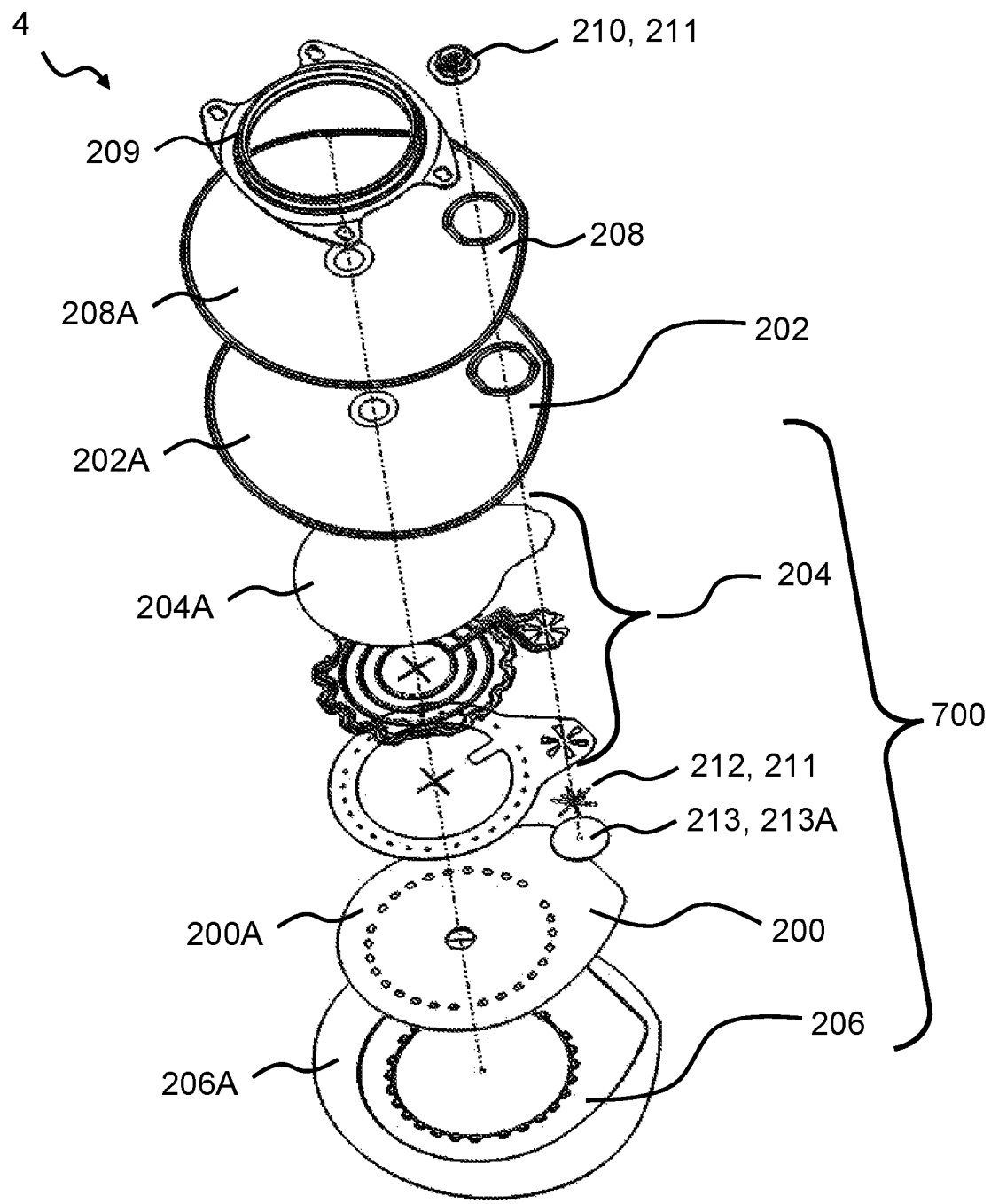
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
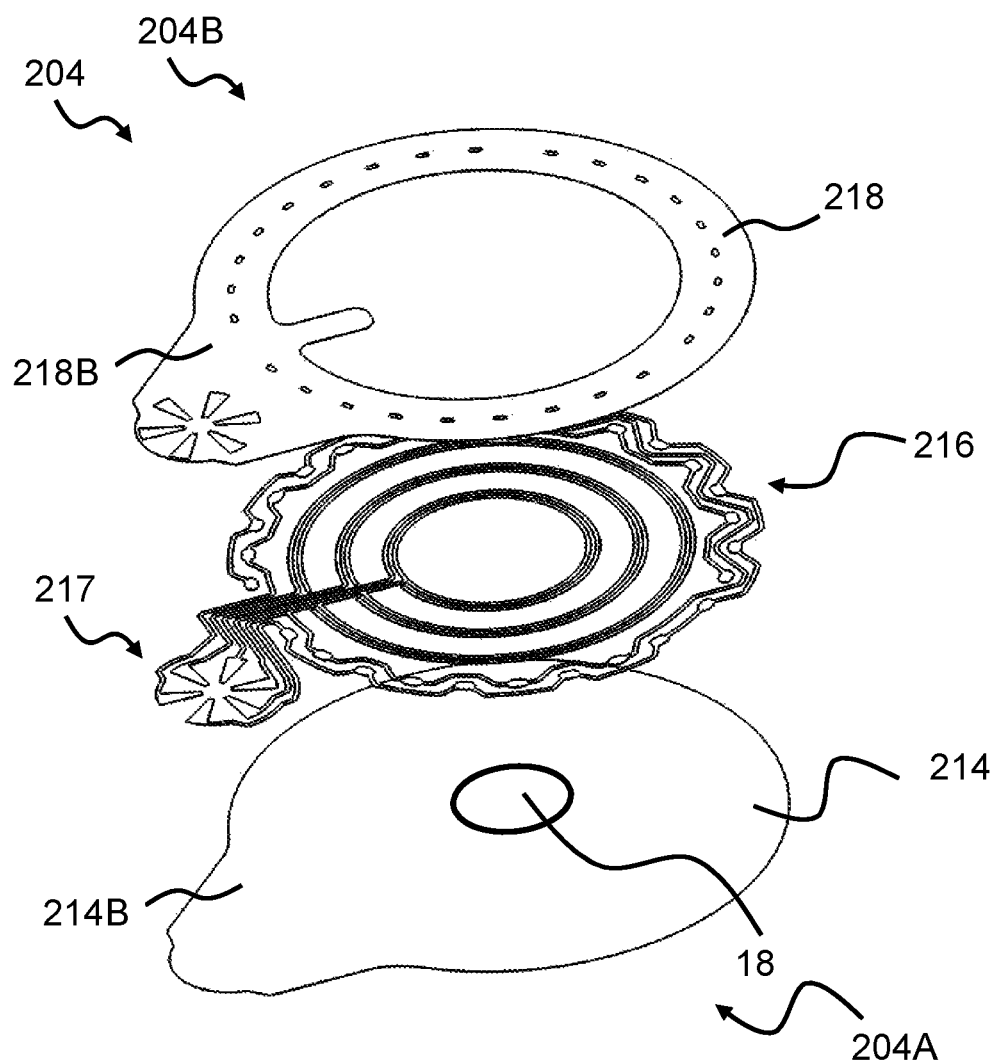
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly comprises a support layer 214 with proximal surface 214B and electrodes 216 including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are provided, such as formed, on a proximal side 214B of the support layer 214, e.g. the electrodes 216 may be positioned on the proximal side 214B of the support layer. Further, electrode assembly 204 comprises a masking element 218 with proximal surface 218B and configured to insulate electrode parts of electrodes 216 from the first adhesive layer of the base plate and/or the sensor assembly part. The masking element 218 covers or overlap with parts of the electrodes 216 when seen in the axial direction.

Figure 5:
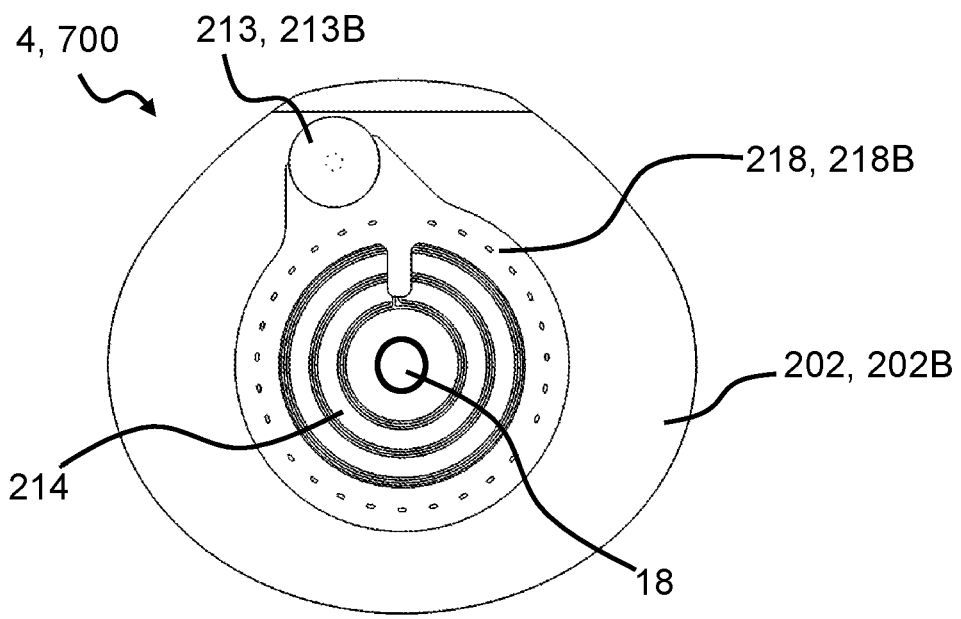
FIG. 5 is a proximal view of parts of a base plate and/or a sensor assembly part.

FIG. 5 is a proximal view of proximal surfaces of base plate parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 and/or of the sensor assembly part 700 when seen in the axial direction and protects the first adhesive layer from mechanical stress from the terminal elements of the base plate and/or the sensor assembly part.

Figure 6:
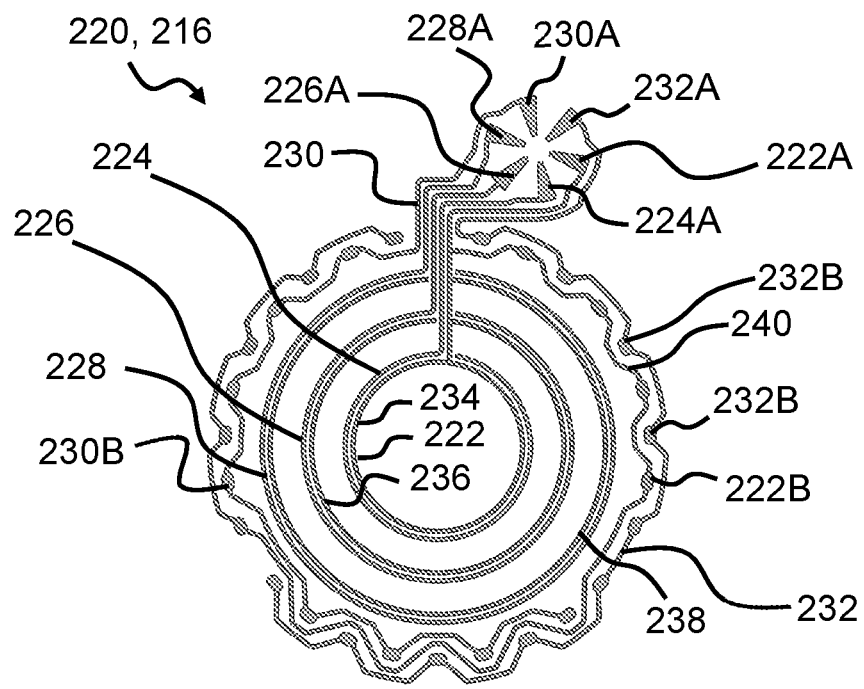
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
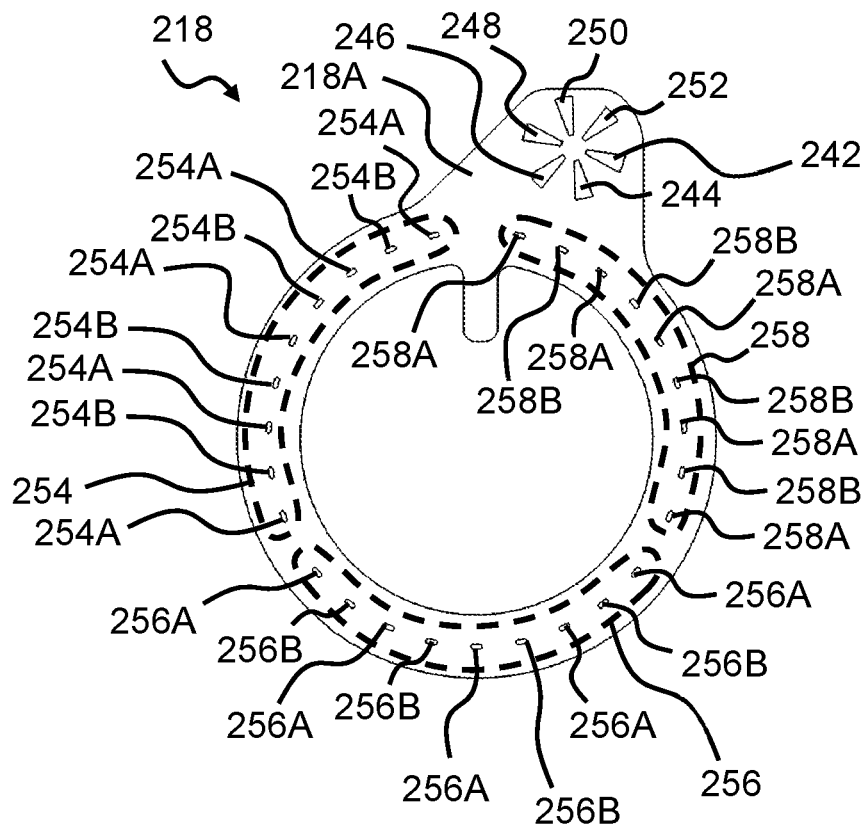
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
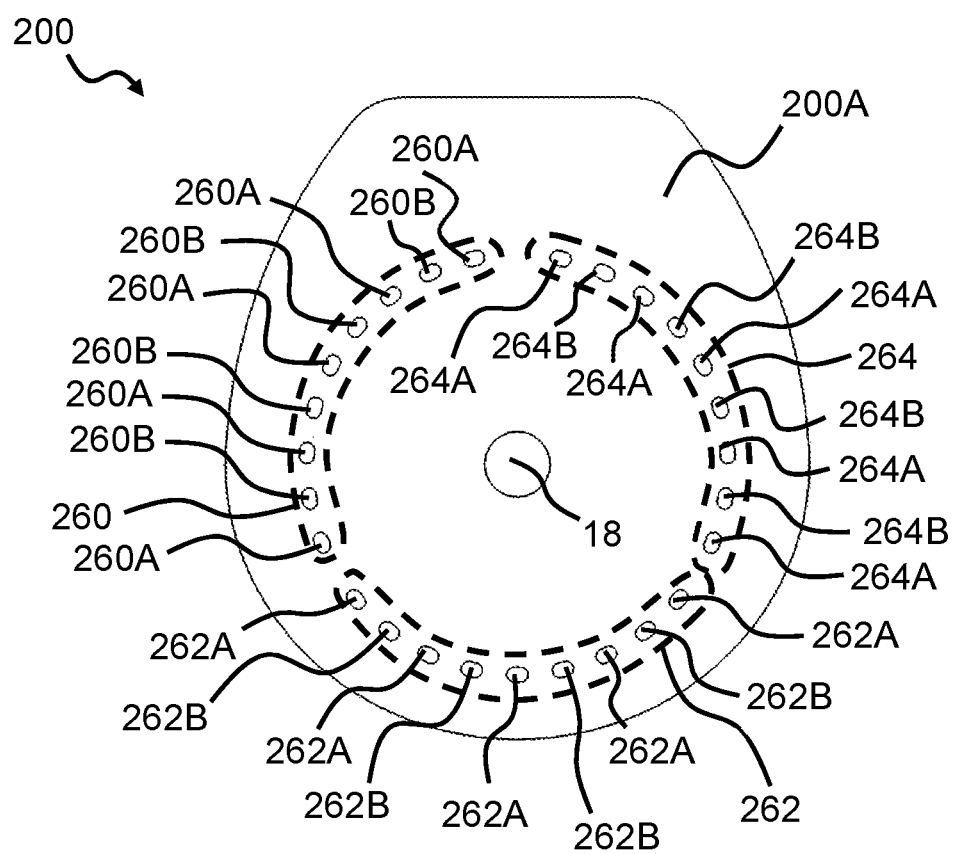
FIG. 8 is a distal view of an exemplary first adhesive layer.
Figure 9:
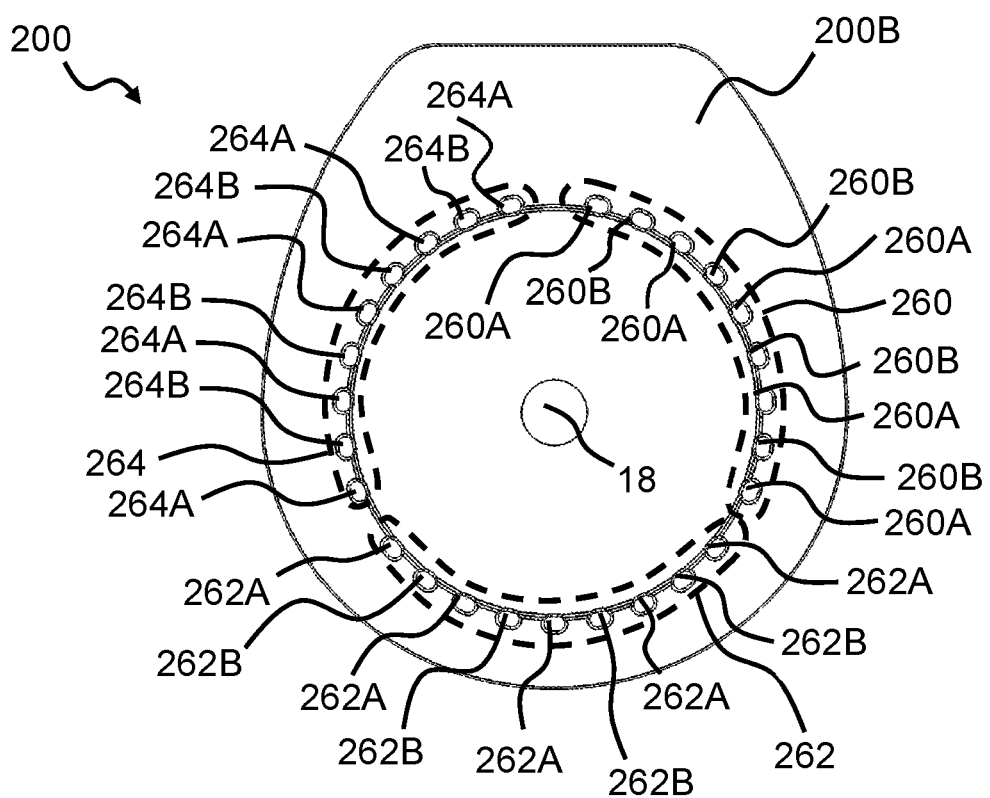
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
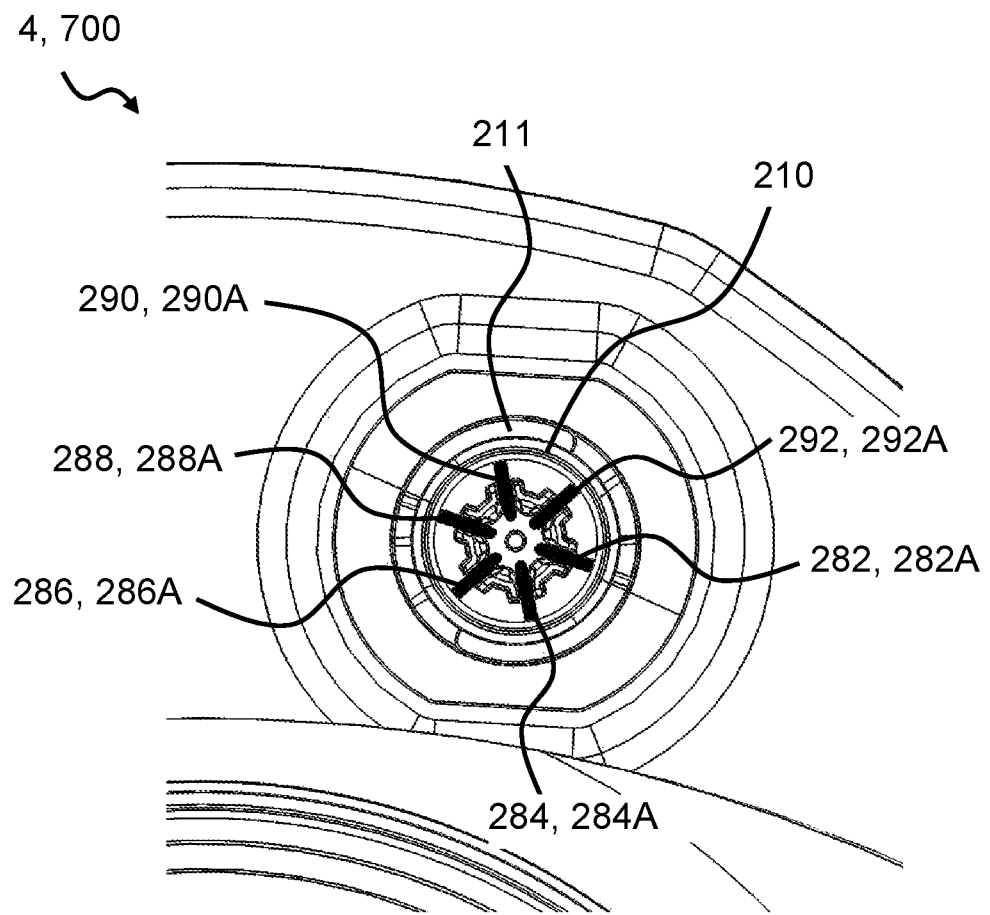
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate and/or the sensor assembly part and thus forming a releasable coupling. The first connector 211 of the monitor interface comprises a plurality of terminals formed by respective terminal elements for forming respective electrical connections with respective terminals of the monitor device.

The plurality of terminals of the first connector 211/ monitor interface comprises a ground terminal element 282 forming a ground terminal 282A, a first terminal element 284 forming a first terminal 284A, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

Figure 11:
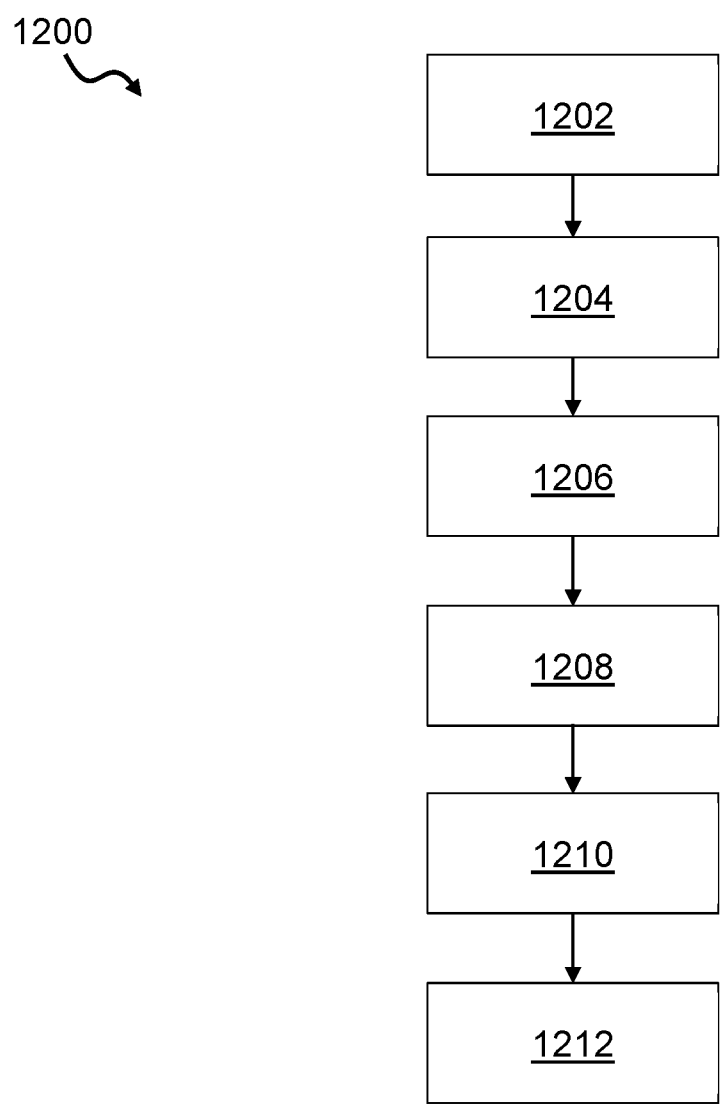
FIG. 11 shows a flow diagram of an exemplary method for manufacturing.

FIG. 11 shows a flow diagram of an exemplary method 1200 for manufacturing a base plate, such as a base plate 4 as disclosed in the previous figures, or for manufacturing a sensor assembly part, such as a sensor assembly part 700 as disclosed in the previous figures. For illustrations of the structural features of the base plate and/or sensor assembly part, reference is made to the other figures, in particular FIGS. 3, 4 and 13.

The method 1200 comprises positioning 1202 a coupling part 210. The coupling part 210 defines a terminal interface region 270. For example, the terminal interface region 270 may be a region surrounded by the coupling part 210.

The method 1200 comprises positioning 1204 an electrode assembly 204 having a distal side 204A and a proximal side 204B. The electrode assembly 204 is positioned such that the distal side 204A of the electrode assembly 204 is facing the coupling part 210. The electrode assembly 204 comprises a support layer 214 and one or more electrodes 216 provided on a proximal side 214B of the support layer 214. Each of the one or more electrodes 216 comprises a connection part 217.

The method 1200 comprises positioning 1206 one or more terminal elements 272, e.g. such as the terminal elements 282, 284, 286, 288, 290, 292 of FIG. 10. The one or more terminal elements 272 are positioned 1206 such that a distal part 274A of each of the one or more terminal elements extends into the terminal interface region 270 and a proximal part 274B of each of the one or more terminal elements 272 extends to the proximal side of the electrode assembly 204.

Positioning 1206 the one or more terminal elements 272 may comprise inserting the one or more terminal elements 272 through the electrode assembly 204. The one or more terminal elements 272 may be inserted from the proximal side 204B of the electrode assembly 204. Alternatively, the one or more terminal elements 272 may be inserted from the distal side 204A of the electrode assembly 204. The one or more terminal elements 272, such as a distal end 272B or a proximal end 272A of each of the one or more terminal elements 272, may be used in inserting the one or more terminal elements 272 to penetrate the electrode assembly 204. The one or more terminal elements 272 may be inserted through the support layer 214 of the electrode assembly 204, such as without penetrating the electrodes 216 of the electrode assembly 204. Alternatively, the one or more terminal elements 272 may be inserted through the respective connection parts 217.

The method 1200 comprises affixing 1208 the proximal part 274B of each of the one or more terminal elements 272 to respective connection parts 217 of the one or more electrodes 216. Affixing 1208 the one or more terminal elements 272 may comprise positioning the proximal part 274B of each of the one or more terminal elements 272 to contact respective connection parts 217 of the one or more electrodes 216.

Affixing 1208 the proximal part 274B of the one or more terminal elements 272 to the respective connection parts 217 of the one or more electrodes 216 may comprise bonding, such as gluing, e.g. using conductive glue, or soldering, the proximal part 274B of each of the one or more terminal elements 272 to the respective connection parts 217 of the one or more electrodes 216.

For example, affixing 1208 the proximal part 274B of each of the one or more terminal elements 272 to the respective connection parts 217 of the one or more electrodes 216 may comprise providing an affixing material, e.g. solder or glue, such as an electrically conductive glue, for affixing the proximal part 274B of each of the one or more terminal elements 272 to the respective connection parts 217 of the one or more electrodes 216. For example, a conductive glue may be provided between the proximal part 274B of each of the one or more terminal elements 272 and the respective connection parts 217 of the one or more electrodes 216. Affixing 1208 the proximal part 274B of each of the one or more terminal elements 272 to the respective connection parts 217 of the one or more electrodes 216 may comprise curing of an affixing material, e.g. uv-curing, thermal curing, etc.

Alternatively or additionally, affixing 1208 the proximal part 274B of each of the one or more terminal elements 272 to the respective connection parts 217 of the one or more electrodes 216 may comprise soldering the proximal part 274B of each of the one or more terminal elements 272 to the respective connection parts 217 of the one or more electrodes 216.

The method 1200 comprises securing 1210 the distal part 274A of each of the one or more terminal elements 272 to the coupling part 210. Securing 1210 the distal part 274A of each of the one or more terminal elements 272 to the coupling part 210 may comprise positioning the distal part 274A of each of the one or more terminal elements 272 to contact a surface, such as a distal surface, of the coupling part 210. For example, the one or more terminal elements 272 may be bent such that the distal part 274A of each of the one or more terminal elements 272 is contacting the surface of the coupling part 210. Alternatively or additionally, the distal part 274A may be secured to the coupling part 210 by engaging with a clamping element of the coupling part 210.

Affixing 1208 the proximal part 274B of each of the one or more terminal elements 272 and securing 1210 the distal part 274A of each of the one or more terminal elements 272 to the coupling part 210 may be performed simultaneously, such as performed by the same action. For example, positioning the distal part 274A of each of the one or more terminal elements 272 to contact the surface of the coupling part 210 may result in the proximal part 274B of each of the one or more terminal elements 272 to be affixed to the respective connection parts 217 of the one or more electrodes 216.

The method 1200 further comprises an optional step of positioning 1212 a first adhesive layer 200. The first adhesive layer 200 comprises a distal side and a proximal side. The first adhesive layer 200 is positioned 1212 such that the distal side of the first adhesive layer 200 is facing the proximal side of the electrode assembly 204. The first adhesive layer 200 may be positioned 1212 after affixing 1208 the proximal part 274B of each of the one or more terminal elements 272 to the respective connection parts 217 of the one or more electrodes 216, e.g. such that he proximal parts 274B are located between the first adhesive layer 200 and the electrode assembly 204.

The first adhesive layer 200 may be positioned 1212 together with a release liner 206 provided on the proximal side of the first adhesive layer 200. The first adhesive layer 200 may be formed on the release liner 206 by scraping a thin layer of a first adhesive composition onto the release liner 206 to form the first adhesive layer 200. The first adhesive layer 200 may be formed on the release liner prior to positioning 1212 the first adhesive layer 200, e.g. with the release liner 206.

The method 1200 provides that an electrical connection is provided from the distal side of the base plate 4 and/or the sensor assembly part 700 to the electrodes 216 of the electrode assembly 204 being positioned on a proximal facing side of the electrode assembly 204. The proximal position of the electrodes 216 may provide for better measuring of leakage and/or wear of the base plate. The method 1200 further provides that the electrical connection between the terminal elements 272 and the electrodes may be maintained, even if the thickness of any intermediary material, such as the electrode assembly, should be reduced, e.g. due to viscous flow of the intermediary material.

Figure 12:
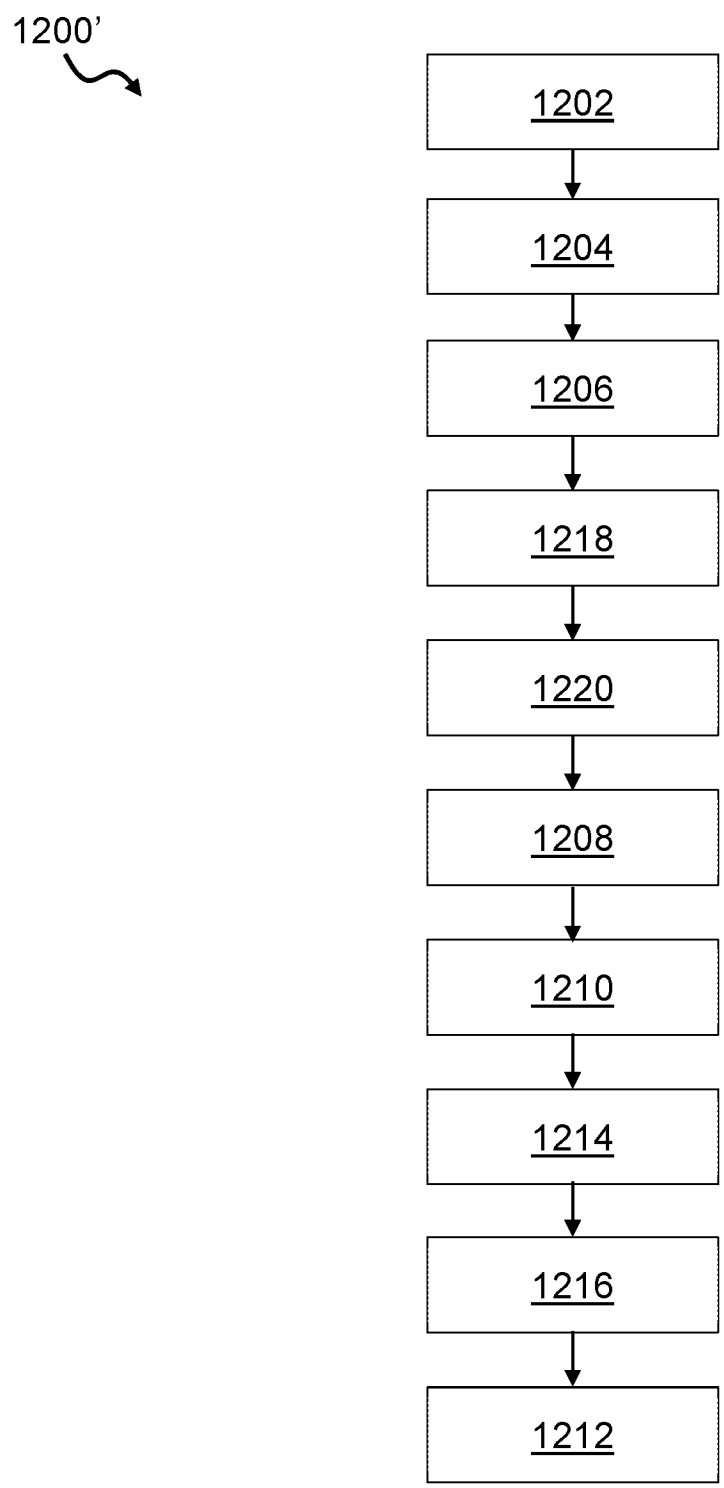
FIG. 12 shows a flow diagram of an exemplary method for manufacturing, FIG. 13a) and FIG 13b) schematically illustrate the positioning, affixing and/or securing of terminal elements FIG. 13c) schematically illustrates insertion of terminal elements, FIG. 14 schematically illustrates a base plate and/or a sensor assembly part, FIG. 15 schematically illustrates a base plate and/or a sensor assembly part.

FIG. 12 shows a flow diagram of an exemplary method 1200' for manufacturing a base plate, such as a base plate 4 as disclosed in the previous figures, or for manufacturing a sensor assembly part, such as a sensor assembly part 700 as disclosed in the previous figures. For illustrations of the structural features of the base plate and/or the sensor assembly part, reference is made to the other figures, in particular FIGS. 3, 4 and 13.

The method 1200' comprises the same steps as the method 1200 as explained in relation to FIG. 11, namely, positioning 1202 a coupling part 210, positioning 1204 an electrode assembly 204, positioning 1206 one or more terminal elements 272, affixing 1208 the proximal part 276B to respective connection parts 217, securing 1210 the distal parts 276A to the coupling part 210, and optionally positioning 1212 a first adhesive layer 200. The additional steps of the method 1200' as described in the following are generally not mutually dependent, and hence may be individually applied and/or omitted.

The method 1200' comprises positioning 1214 a top layer 208. The top layer 208 has a distal side and a proximal side. The top layer 208 is positioned 1214 such that the distal side of the top layer 208 is facing the coupling part and the proximal side of the top layer 208 is facing the distal side of the electrode assembly 204.

The method 1200' comprises positioning 1216 a second adhesive layer 202. The second adhesive layer 202 has a distal side and a proximal side. The second adhesive layer is positioned 1216 such that the distal side of the second adhesive layer 202 is facing the coupling part and the proximal side of the second adhesive layer 202 is facing the distal side of the electrode assembly 204. The second adhesive layer 202 may be positioned 1216 on the top layer 208, e.g. after the top layer 208 is positioned 1214. The second adhesive layer 202 may be positioned 1216 on the top layer 208 by scraping a thin layer of a second adhesive composition onto the top layer 208 to form the second adhesive layer 202. Positioning 1214 the top layer 208 and positioning 1216 the second adhesive layer may be performed simultaneously.

The second adhesive layer 202 may be positioned 1216 prior to positioning 1206 the one or more terminal elements 272 and/or the top layer 208 may be positioned 1214 prior to positioning 1206 the one or more terminal elements 272. Positioning 1206 the one or more terminal elements 272 may comprise inserting the one or more terminal elements 272 through the second adhesive layer 202 and/or the top layer 208. The one or more terminal elements 272, such as a distal end or a proximal end of each of the one or more terminal elements 272, may be used in inserting the one or more terminal elements 272 to penetrate the electrode assembly 202, the second adhesive layer 202 and/or the top layer 208.

The method 1200' comprises providing 1218 each of the one or more terminal elements 272 with a proximal terminal element bend 276B. For example, providing 1218 proximal terminal element bend(s) may comprise forming a proximal terminal element bend on each of the one or more terminal elements 272. A proximal terminal element bend 276B may provide that the proximal part 274B of each of the one or more terminal element 272 contact the respective connection parts 217 of the one or more electrodes 216. Providing 1014 each of the one or more terminal elements 272 with a proximal terminal element bend 276B may in particular be advantageous to provide an electrical connection between the terminal elements 272 and the respective connection parts 217, if the terminal elements 272 are penetrating the support layer 214 and not penetrating the electrodes 216. Providing 1218 proximal terminal element bend(s) 276B may be an integrated step in affixing 1208 the proximal parts 274B and the respective connection parts 217. For example, an affixing material 296, e.g. solder or glue, such as an electrically conductive glue, may be added to the connection parts 217, and in providing 1218 proximal terminal element bends 276B, the proximal parts 274B may be brought into contact with the affixing material 296. Providing 1218 each of the one or more terminal elements 272 with a proximal terminal element bend 276B may be performed after positioning 1206 the one or more terminal elements 272. Alternatively, providing 1218 the proximal terminal element bend(s) 276B may be performed prior to positioning 1206 the one or more terminal elements 272. Providing 1218 the proximal terminal element bend(s) 276B may be performed prior to affixing 1208 the proximal part 274B to the respective connection parts 217.

The method 1200' comprises providing 1220 each of the one or more terminal elements 272 with a distal terminal element bend 276A. For example, providing 1220 distal terminal element bend(s) may comprise forming a distal terminal element bend to each of the one or more terminal elements 272. Providing 1220 each of the one or more terminal elements 272 with a distal terminal element bend 276A may be provided to position the distal part 274A of each of the one or more terminal elements 272 to contact the distal surface of the coupling part 210, e.g. to secure the distal part 274A of each of the one or more terminal elements 272 to the coupling part 210. Providing 1220 distal terminal element bend(s) may be an integrated step in securing 1210 the distal part 274A of each of the one or more terminal elements 272 to the coupling part 210. Alternatively, providing 1220 the distal terminal element bend(s) 276A may be performed after positioning 1206 the one or more terminal elements 272. Alternatively, providing 1220 the distal terminal element bend(s) 276A may be performed prior to positioning 1206 the one or more terminal elements 272.

Figure 13:
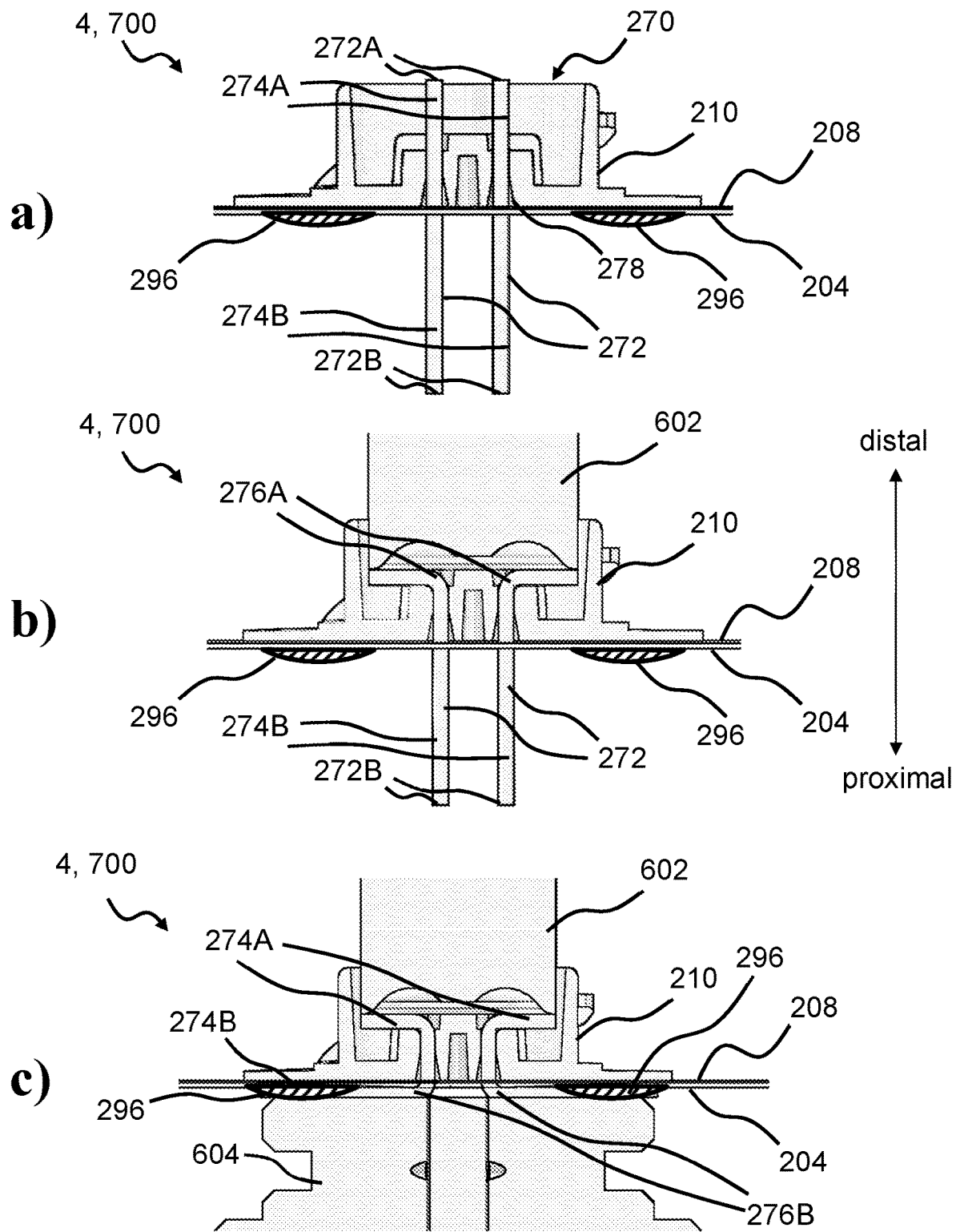

FIG. 13 schematically illustrates positioning, affixing and/or securing of terminal elements 272, such as in an exemplary method, such as the method 1200 and/or 1200' of FIGS. 11 and 12.

A coupling part 210, a top layer 208 and an electrode assembly 204 are positioned such that a distal side of the electrode assembly 204 is facing the coupling part 210, and such that the top layer 208 is between the coupling part 210 and the electrode assembly 204. A second adhesive layer (not shown) may be positioned between the top layer 208 and the electrode assembly 204.

In FIG. 13a, terminal elements 272 are inserted through the electrode assembly from the proximal side towards the distal side of the base plate 4 and/or the sensor assembly part 700. The terminal elements 272 are straight pins, e.g. from a longer strand of material.

The terminal elements 272 may for example be gold plated copper. The terminal elements 272 have a distal end 272A and a proximal end 272B. The terminal elements 272 may be inserted by penetrating the electrode assembly 204 and the top layer 208 with the distal end 272A of the terminal elements 272 from the proximal side to the distal side of the base plate 4 and/or the sensor assembly part 700. A distal part 274A of the terminal elements 272 are extending into a terminal interface region 270 defined by the coupling part 210. The terminal elements 272 may be extending through respective connection parts of the electrodes of the electrode assembly 204. Alternatively, the terminal elements 272 may be extending through the electrode assembly 204 without extending though electrodes or connection parts of electrodes, e.g. the terminal elements 272 may be extending through a support layer of the electrode assembly 204 without extending though electrodes or connection parts of electrodes.

The coupling part 210 comprises guide holes 278 for receiving terminal elements 272 being inserted through the coupling part 210 from the proximal side. The guide holes 278 may facilitate positioning of the terminal elements 272.

As shown in FIG. 13b, an affixing material 296, e.g. solder or glue, such as conductive glue, is provided to the proximal side of the connection parts of the electrodes of the electrode assembly 204.

After inserting the terminal elements 272 through the electrode assembly 204 and the top layer 208, the terminal elements 272 are provided with distal terminal element bends 276A, as shown in FIG. 13b. The distal terminal element bends 276A is provided by positioning a distal staple element 602 on the distal side of the coupling part 210. The distal staple element 602 comprises curvatures such that upon movement of the terminal elements 272 in a distal direction, the distal end 272A of the terminal elements 272 are guided in a direction perpendicular to the distal direction. Thereby, the terminal elements 272 are provided with distal terminal element bends 276A. Thereby, the terminal elements 272 may be secured to the coupling part 210.

The terminal elements 272 are provided with proximal terminal element bends 276B, as shown in FIG. 13c. The proximal terminal element bends 276B are provided by positioning a proximal staple element 604 on the proximal side of the base plate 4 and/or the sensor assembly part 700. The proximal staple element 604 is configured to guide the proximal part 274B of each of the terminal elements 272 in a direction perpendicular to the distal direction and to press the proximal part 274B of each of the terminal elements 272 towards the coupling part 210, such as in a distal direction. Thereby, the terminal elements 272 are provided with proximal terminal element bends 276B. The distal staple element 602 provides a counter force. The distal part 274A and the proximal part 274B of each of the terminal elements 272 are pressed towards each other by the distal staple element 602 and the proximal staple element 604, and the coupling part 210, the top layer 208 and the electrode assembly 204 are clamped between the proximal parts 274B and distal parts 274A of the terminal elements 272.

Although illustrated as separate steps, the distal terminal element bend 276A and the proximal terminal element bend 276B may be provided simultaneously or almost simultaneously, e.g. the distal staple element 602 and the proximal staple element 604 may be engaging simultaneously or almost simultaneously. Thereby, the process will proceed from the situation as illustrated in FIG. 13a to the situation as illustrated in FIG. 13c.

In providing the terminal elements 272 with the proximal terminal bends 276B the proximal parts 274B may be brought into contact with connection parts of electrodes of the electrode assembly, such as to electrically connect the terminal elements 272 with respective electrodes, such as connection parts of the electrodes. Furthermore, in providing the terminal elements 272 with the proximal terminal bends 276B the proximal parts 274B are brought into contact with the affixing material 296. Thereby, the proximal parts 274B and the electrodes and/or the connection parts of the electrodes may be affixed, such as bonded, together.

Figure 14:
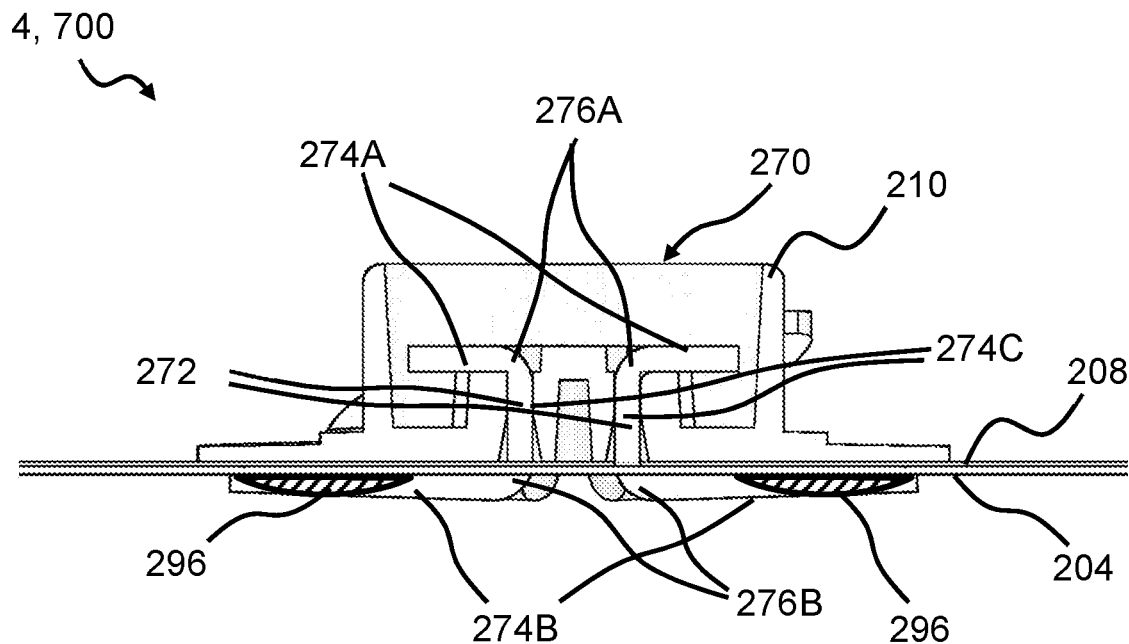

FIG. 14 schematically illustrates a base plate 4 and/or a sensor assembly part 700 comprising a coupling part 210. The coupling part defines a terminal interface region 270. The base plate 4 and/or the sensor assembly part 700 comprises an electrode assembly 204 having a distal side and a proximal side. The distal side of the electrode assembly 204 is facing the coupling part 210. Terminal elements 272 extends through the electrode assembly 204. Each of the terminal elements have a distal part 274A extending into the terminal interface region 270 and a proximal part 274B extending to the proximal side of the electrode assembly 204. The terminal elements 272 comprises terminal element bends 276A; 276B between the proximal part 274B and the distal part 274A. The terminal elements 272 comprises a distal terminal element bend 276A between the distal part 274A and a centre part 274C of the terminal element 272. The terminal elements 272 comprises a proximal terminal element bend 276B between the proximal part 274A and the centre part 274C of the terminal element 272.

The proximal part 274B of each of the terminal elements 272 are electrically connected to respective connection parts of electrodes of the electrode assembly 204. The proximal part 274B of each of the terminal elements 272 are affixed, by affixing material 296, to the respective connection parts of electrodes of the electrode assembly 204. The affixing material 296 may be a glue, such as a conductive glue. Alternatively or additionally, the affixing material 296 may be solder.

The distal part 274A of each of the terminal elements contact a distal surface of the coupling part 210, e.g. in order to secure the terminal elements 272.

The base plate 4 and/or the sensor assembly part 700 comprises a top layer 208. The top layer 208 has a distal side facing the coupling part 210 and a proximal side facing the distal side of the electrode assembly 204. The terminal elements 272 are extending through the top layer 208. If the base plate and/or the sensor assembly part had a second adhesive layer, as described in relation to other figures, the proximal side of the top layer 208 may be facing the second adhesive layer.

The base plate and/or the sensor assembly part as illustrated in FIG. 14 may be provided by the steps as explained in relation to FIG. 13. Hence, FIG. 14 may be following FIG. 13c.

Figure 15:
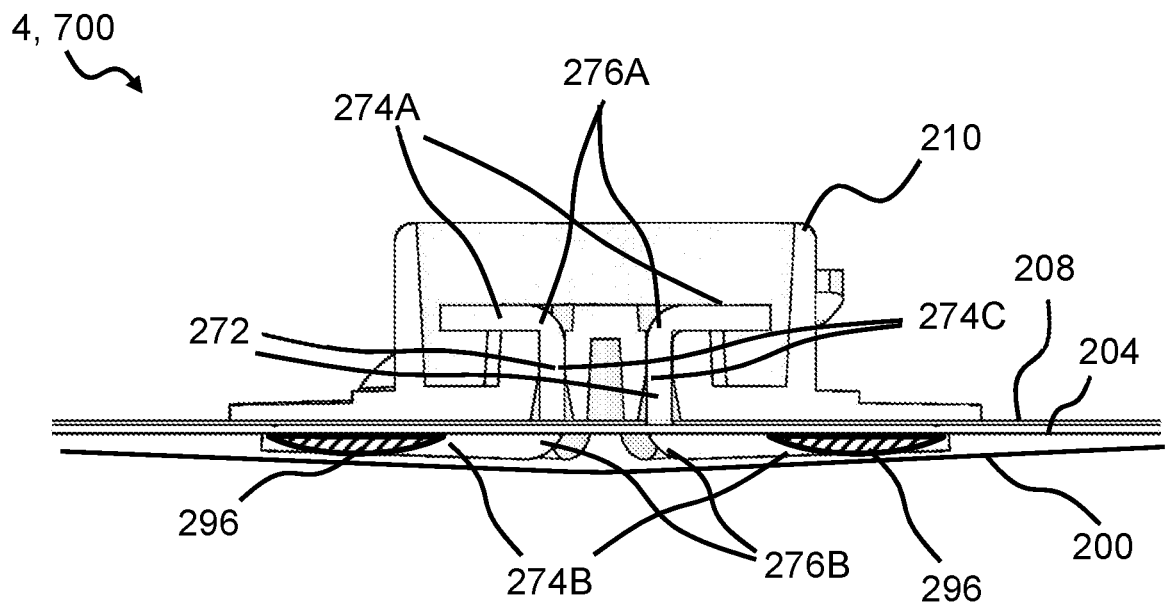

FIG. 15 schematically illustrates a base plate 4 and/or the sensor assembly part 700, such as the base plate 4 and/or the sensor assembly part 700 as illustrated in FIG. 14, with the addition as compared to FIG. 14, that a first adhesive layer 200 has been added. The first adhesive layer 200 has a distal side facing the proximal side of the electrode assembly 204. The proximal part 274B of each of the terminal elements 272 are located between the first adhesive layer 200 and the electrode assembly 204. Thus, the first adhesive layer 200 may have been added to the base plate 4 and/or the sensor assembly part 700 after the terminal elements 272 have been positioned, affixed and/or secured.

The position of the first connector on the base plate and/or the sensor assembly part, the number of terminals and the position of the terminals in the coupling part may be adapted to the electrode configuration used in the electrode assembly of the base plate and/or the sensor assembly part.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments of the present disclosure is set out in the following items:

1. Method for manufacturing a base plate or a sensor assembly part for an ostomy appliance, the method comprising:
   positioning a coupling part, the coupling part defining a terminal interface region;
   positioning an electrode assembly having a distal side and a proximal side, wherein the electrode assembly is positioned such that the distal side of the electrode assembly is facing the coupling part, the electrode assembly comprises a support layer and one or more electrodes provided on a proximal side of the support layer, each of the one or more electrodes comprising a connection part;
   positioning one or more terminal elements such that a distal part of each of the one or more terminal elements extends into the terminal interface region and a proximal part of each of the one or more terminal elements extends to the proximal side of the electrode assembly;
   affixing the proximal part of each of the one or more terminal elements to respective connection parts of the one or more electrodes;
   securing the distal part of each of the one or more terminal elements to the coupling part.

2. Method according to item 1 comprising positioning a first adhesive layer with a distal side facing the proximal side of the electrode assembly, wherein the first adhesive layer is positioned after positioning the one or more terminal elements such that the proximal part of each of the one or more terminal is located between the first adhesive layer and the electrode assembly.

3. Method according to any of items 1 or 2 comprising positioning a second adhesive layer with a distal side facing the coupling part and a proximal side facing the distal side of the electrode assembly.

4. Method according to any of items 1-3 comprising positioning a top layer with a distal side facing the coupling part and a proximal side facing the distal side of the electrode assembly.

5. Method according to any of the preceding items comprising providing each of the one or more terminal elements with a proximal terminal element bend prior to affixing the proximal part of each of the one or more terminal elements to the respective connection parts of respective electrodes of the one or more electrodes.

6. Method according to any of the preceding items, wherein positioning the one or more terminal elements comprises inserting the one or more terminal elements through the respective connection parts of the one or more electrodes.

7. Method according to any of the preceding items, wherein securing the distal part of each of the one or more terminal elements to the coupling part comprises positioning the distal part of each of the one or more terminal element to contact a distal surface of the coupling part.

8. Method according to item 7, wherein each of the one or more terminal elements is provided with a distal terminal element bend to position the distal part of each of the one or more terminal elements to contact the distal surface of the coupling part 9. Method according to any of the preceding items wherein affixing the proximal part of each of the one or more terminal elements to the respective connection parts of the one or more electrodes comprises providing an electrically conductive glue affixing the proximal part of each of the one or more terminal elements to the respective connection parts of the one or more electrodes.

10. Method according to any of the preceding items wherein affixing the proximal part of each of the one or more terminal elements to the respective connection parts of the one or more electrodes comprises soldering the proximal part of each of the one or more terminal elements to the respective connection parts of the one or more electrodes.

11. Sensor assembly part for an ostomy appliance, the sensor assembly part comprising:
a coupling part defining a terminal interface region;
an electrode assembly having a distal side and a proximal side, the distal side of the electrode assembly facing the coupling part, the electrode assembly comprises a support layer and one or more electrodes provided on a proximal side of the support layer, each of the one or more electrodes comprising a connection part;
one or more terminal elements with a distal part extending into the terminal interface region and a proximal part extending to the proximal side of the electrode assembly;
wherein the proximal part of each of the one or more terminal elements are affixed to respective connection parts of the one or more electrodes, and the distal part of each of the one or more terminal elements are secured to the coupling part.

12. Sensor assembly part according to item 11 comprising a first adhesive layer with a distal side facing the proximal side of the electrode assembly, and wherein the proximal part of each of the one or more terminal is located between the first adhesive layer and the electrode assembly.

13. Sensor assembly part according to any of items 11 or 12 comprising a second adhesive layer with a distal side facing the coupling part and a proximal side facing the distal side of the electrode assembly.

14. Sensor assembly part according to any of items 11-13 comprising a top layer with a distal side facing the coupling part and a proximal side facing the distal side of the electrode assembly.

15. Sensor assembly part according to any of items 11-14, wherein the distal part of each of the one or more terminal elements are secured to a distal surface of the coupling part.

16. Sensor assembly part according to any of items 11-15, wherein the proximal part of each of the one or more terminal elements are affixed to the respective connection parts with an electrically conductive glue.

17. Sensor assembly part according to any of items 11-16, wherein the proximal part of each of the one or more terminal elements are affixed to the respective connection parts with solder.

18. Base plate for an ostomy appliance, the base plate comprising:
a coupling part defining a terminal interface region;
an electrode assembly having a distal side and a proximal side, the distal side of the electrode assembly facing the coupling part, the electrode assembly comprises a support layer and one or more electrodes provided on a proximal side of the support layer, each of the one or more electrodes comprising a connection part;
one or more terminal elements with a distal part extending into the terminal interface region and a proximal part extending to the proximal side of the electrode assembly;
wherein the proximal part of each of the one or more terminal elements are affixed to respective connection parts of the one or more electrodes, and the distal part of each of the one or more terminal elements are secured to the coupling part.

19. Base plate according to item 18 comprising a first adhesive layer with a distal side facing the proximal side of the electrode assembly, and wherein the proximal part of each of the one or more terminal is located between the first adhesive layer and the electrode assembly.

20. Base plate according to any of items 18 or 19 comprising a second adhesive layer with a distal side facing the coupling part and a proximal side facing the distal side of the electrode assembly.

21. Base plate according to any of items 18-20 comprising a top layer with a distal side facing the coupling part and a proximal side facing the distal side of the electrode assembly.

22. Base plate according to any of items 18-21, wherein the distal part of each of the one or more terminal elements are secured to a distal surface of the coupling part.

23. Base plate according to any of items 18-22, wherein the proximal part of each of the one or more terminal elements are affixed to the respective connection parts with an electrically conductive glue.

24. Base plate according to any of items 18-23, wherein the proximal part of each of the one or more terminal elements are affixed to the respective connection parts with solder.

LIST OF REFERENCES 1 ostomy system
2 ostomy appliance
4 base plate
6 monitor device
8 accessory device 10 server device
12 network
14 coupling member
16 coupling ring
18 stoma-receiving opening
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
122 antenna
124 wireless transceiver
126 loudspeaker
128 haptic feedback element
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection part(s)
218 masking element
218A distal surface of masking element
218B proximal surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
270 terminal interface region
272 terminal element(s)
272A distal end of terminal element(s)
272B proximal end of terminal element(s)
274A distal part of terminal element(s)
274B proximal part of terminal element(s)
276A distal terminal element bend
276B proximal terminal element bend
278 guide hole
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
296 affixing material
602 distal staple element
604 proximal staple element
700 sensor assembly part
M number of terminals in the first interface of the monitor device

The invention claimed is:

1. Method for manufacturing a base plate for a medical appliance, the method comprising:
positioning a coupling part, the coupling part defining a terminal interface region;
positioning an electrode assembly having a distal side and a proximal side, wherein the electrode assembly is positioned such that the distal side of the electrode assembly is facing the coupling part, the electrode assembly comprising a support layer and one or more electrodes provided on a proximal side of the support layer, each of the one or more electrodes comprising a connection part;

positioning one or more terminal elements such that a distal part of each of the one or more terminal elements extends into the terminal interface region and a proximal part of each of the one or more terminal elements extends to the proximal side of the electrode assembly;

affixing the proximal part of each of the one or more terminal elements to respective connection parts of the one or more electrodes such that connection between the one or more terminal elements and respective connection parts is maintained in the absence of external forces forcing the terminal elements and the respective connection parts together;

securing the distal part of each of the one or more terminal elements to the coupling part; and positioning a first adhesive layer with a distal side facing the proximal side of the electrode assembly by positioning the first adhesive layer after positioning the one or more terminal elements such that the proximal part of each of the one or more terminal elements is located between the first adhesive layer and the electrode assembly, the first adhesive layer comprising one or more water soluble or water swellable hydrocolloids.

2. The method according to claim 1, wherein the support layer comprises a support layer stomal opening and the first adhesive layer further comprises a first adhesive stomal opening, and wherein the step of positioning the first adhesive layer comprises aligning the support layer stomal opening and the first adhesive stomal opening to form a stomal opening of the base plate configured to allow passage of output from a stoma of a user.

3. The method according to claim 1, further comprising a step of positioning a second adhesive layer with a distal side facing the coupling part and a proximal side facing the distal side of the electrode assembly, the second adhesive layer comprising one or more water soluble or water swellable hydrocolloids.

4. The method according to claim 1, further comprising a step of positioning a top layer with a distal side facing the coupling part and a proximal side facing the distal side of the electrode assembly.

5. The method according to claim 1, further comprising a step of providing each of the one or more terminal elements with a proximal terminal element bend prior to affixing the proximal part of each of the one or more terminal elements to the respective connection parts of respective electrodes of the one or more electrodes.

6. The method according to claim 1, wherein the step of positioning the one or more terminal elements comprises inserting the one or more terminal elements through the respective connection parts of the one or more electrodes.

7. The method according to claim 1, wherein the step of securing the distal part of each of the one or more terminal elements to the coupling part comprises positioning the distal part of each of the one or more terminal element to contact a distal surface of the coupling part.

8. The method according to claim 7, wherein each of the one or more terminal elements is provided with a distal terminal element bend to position the distal part of each of the one or more terminal elements to contact the distal surface of the coupling part.

9. The method according to claim 1, wherein the step of affixing the proximal part of each of the one or more terminal elements to the respective connection parts of the one or more electrodes comprises providing an electrically conductive glue affixing the proximal part of each of the one or more terminal elements to the respective connection parts of the one or more electrodes.

10. The method according to claim 1, wherein the step of affixing the proximal part of each of the one or more terminal elements to the respective connection parts of the one or more electrodes comprises soldering the proximal part of each of the one or more terminal elements to the respective connection parts of the one or more electrodes.

11. Base plate for a medical appliance, the base plate comprising:

a coupling part defining a terminal interface region;

an electrode assembly having a distal side and a proximal side, the distal side of the electrode assembly facing the coupling part, the electrode assembly comprising a support layer and one or more electrodes provided on a proximal side of the support layer, each of the one or more electrodes comprising a connection part;

one or more terminal elements with a distal part extending into the terminal interface region and a proximal part extending to the proximal side of the electrode assembly; and a first adhesive layer with a distal side facing the proximal side of the electrode assembly, and wherein the proximal part of each of the one or more terminal elements are located between the first adhesive layer and the electrode assembly, the first adhesive layer comprising one or more water soluble or water swellable hydrocolloids, wherein the proximal part of each of the one or more terminal elements are affixed to respective connection parts of the one or more electrodes such that connection between the one or more terminal elements and respective connection parts is maintained in the absence of external forces forcing the terminal elements and the respective connection parts together, and the distal part of each of the one or more terminal elements are secured to the coupling part.

12. The base plate according to claim 11, further comprising a stomal opening at least partly formed by a support layer stomal opening of the support layer and a first adhesive stomal opening of the first adhesive layer, the stomal opening of the base plate being configured to allow passage of output from a stoma of a user.

13. The base plate according to claim 11, further comprising a second adhesive layer with a distal side facing the coupling part and a proximal side facing the distal side of the electrode assembly, the second adhesive layer comprising one or more water soluble or water swellable hydrocolloids.

14. The base plate according to claim 11, further comprising a top layer with a distal side facing the coupling part and a proximal side facing the distal side of the electrode assembly.

15. The base plate according to claim 11, wherein the distal part of each of the one or more terminal elements is secured to a distal surface of the coupling part.

16. The base plate according to claim 11, wherein the proximal part of each of the one or more terminal elements is affixed to the respective connection parts with an electrically conductive glue.

17. The base plate according to claim 11, wherein the proximal part of each of the one or more terminal elements is affixed to the respective connection parts with solder.

* * * * *